(12) United States Patent
Abouabdellah et al.

(10) Patent No.: US 8,697,883 B2
(45) Date of Patent: Apr. 15, 2014

(54) CYCLOPENTA[C]PYRROLE-2-CARBOXYLATE DERIVATIVES, PREPARATION THEREOF AND THERAPEUTIC USE THEREOF

(75) Inventors: Ahmed Abouabdellah, Paris (FR); Luc Even, Paris (FR); Aude Fayol, Paris (FR); Julien Vache, Paris (FR); Philippe Yaiche, Paris (FR)

(73) Assignee: Sanofi, Paris (FR)

( * ) Notice: Subject to any disclaimer, the term of this patent is extended or adjusted under 35 U.S.C. 154(b) by 83 days.

(21) Appl. No.: 13/319,908

(22) PCT Filed: May 11, 2010

(86) PCT No.: PCT/FR2010/050913
§ 371 (c)(1),
(2), (4) Date: Dec. 19, 2011

(87) PCT Pub. No.: WO2010/130944
PCT Pub. Date: Nov. 18, 2010

(65) Prior Publication Data
US 2012/0095040 A1    Apr. 19, 2012

(30) Foreign Application Priority Data

May 12, 2009 (FR) .................................. 09 02268

(51) Int. Cl.
*C07D 261/06* (2006.01)
*C07D 277/24* (2006.01)
*A61K 31/403* (2006.01)
*A61K 31/426* (2006.01)

(52) U.S. Cl.
USPC ............ 548/204; 548/248; 514/274; 514/365

(58) Field of Classification Search
USPC ................... 548/311, 204, 248; 514/274, 365
See application file for complete search history.

(56) References Cited

U.S. PATENT DOCUMENTS

2004/0152724 A1    8/2004  Dart et al.
2006/0047114 A1*   3/2006  Wlodecki ..................... 540/602

FOREIGN PATENT DOCUMENTS

JP         2009-40709        2/2009
WO    WO2005/070910 A2      8/2005

OTHER PUBLICATIONS

International Search Report dated Aug. 25, 2010 issued in PCT/FR2010/050913.
International Preliminary Report on Patentability dated Nov. 15, 2011 issued in PCT/FR2010/050913.

* cited by examiner

*Primary Examiner* — Yong Chu
*Assistant Examiner* — Sonya Wright
(74) *Attorney, Agent, or Firm* — Scully, Scott, Murphy & Presser, P.C.

(57) ABSTRACT

The invention relates to cyclopenta[c]pyrrole-2-carboxylate derivatives, to their preparation and to their therapeutic use.

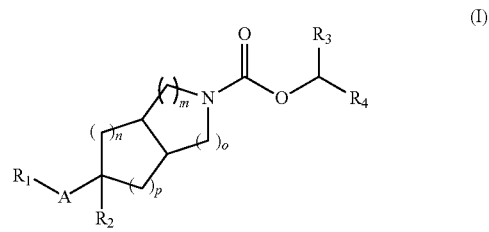

10 Claims, No Drawings

CYCLOPENTA[C]PYRROLE-2-CARBOXYLATE DERIVATIVES, PREPARATION THEREOF AND THERAPEUTIC USE THEREOF

The invention relates to cyclopenta[c]pyrrole-2-carboxylate derivatives, to their preparation and to their therapeutic use.

There is still a need to find and develop products that inhibit the enzyme FAAH (Fatty Acid Amide Hydrolase). The compounds of the invention satisfy this aim.

The compounds of the invention correspond to the general formula (I):

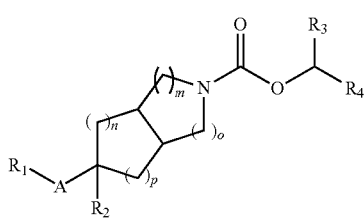

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

m, n, o and p represent, independently of each other, a number ranging from 0 to 3 and are such that each of m+o and n+p is less than or equal to 4;

A represents a covalent bond, an oxygen atom, a group $C_{1-6}$-alkylene or a group —O—$C_{1-6}$-alkylene in which the end represented by an oxygen atom is bonded to the group $R_1$ and the end represented by an alkylene group is bonded to the carbon of the bicycle;

$R_1$ represents a group $R_5$ that is unsubstituted or substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolyl, isoquinolyl, phthalazinyl, quinazolinyl, quinoxalinyl, cinnolinyl, naphthyridinyl, benzothiazolyl, benzoxazolyl, benzimidazolyl, benzisothiazolyl, bensisoxazolyl, indazolyl and benzotriazolyl;

$R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O— ($C_{1-3}$-alkylene)-O— group;

$R_7$ represents a group chosen from phenyl, pyridyl, pyridazinyl, pyrimidinyl, pyrazinyl and triazinyl; the group(s) $R_7$ possibly being substituted with one or more groups $R_6$, which may be identical or different;

$R_3$ represents a hydrogen or fluorine atom, a group $C_{1-6}$-alkyl or a trifluoromethyl group;

$R_4$ represents a 5-membered heterocycle chosen from furyl, pyrrolyl, thienyl, thiazolyl, isothiazolyl, oxazolyl, isoxazolyl, pyrrazolyl, oxadiazolyl, thiadiazolyl, imidazole, triazolyl and tetrazolyl;

this heterocycle being unsubstituted or substituted with one or more substituents chosen from a halogen atom and a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$ or —O— ($C_{1-3}$-alkylene)-O—;

$R_8$, $R_9$, $R_{10}$ and $R_{11}$ represent, independently of each other, a hydrogen atom or a group $C_{1-6}$-alkyl, or form, with the atom(s) that bear them, in the case of $NR_8R_9$, a ring chosen from azetidine, pyrrolidine, piperidine, morpholine, thiomorpholine, azepine, oxazepine and piperazine rings, this ring being optionally substituted with a group $C_{1-6}$-alkyl or benzyl;

in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring.

Among the compounds of general formula (I), a first subgroup of compounds is formed by the compounds for which represents a hydrogen atom or a hydroxyl group. Among the compounds of general formula (I), a second subgroup of compounds is formed by the compounds for which $R_2$ represents a hydrogen atom.

Among the compounds of general formula (I), a third subgroup of compounds is formed by the compounds for which m, n and o have the value 0 or 1, and p has the value 0, 1 or 2.

Among this subgroup, another subgroup of compounds is formed by the compounds for which m, n, o and p have the value 1, or alternatively m and o have the value 1, n has the value 0 and p has the value 2.

Among the compounds of general formula (I), a fourth subgroup of compounds is formed by the compounds for which m, n, o and p have the value 1.

Among the compounds of general formula (I), a fifth subgroup of compounds is formed by the compounds for which A represents a covalent bond or an oxygen atom.

Among the compounds of general formula (I), a sixth subgroup of compounds is formed by the compounds for which A represents an oxygen atom.

Among the compounds of general formula (I), a seventh subgroup of compounds is formed by the compounds for which $R_1$ represents a group $R_5$ that is unsubstituted or substituted with one or more groups $R_6$ and/or $R_7$;

$R_5$ represents a phenyl, naphthyl, benzothiazolyl or isoquinolyl group;

$R_6$ represents a halogen atom, more particularly a fluorine or chlorine atom, or a group $C_{1-6}$-haloalkyl, more particularly trifluoromethyl, or a group $C_{1-6}$-alkoxy, more particularly a methoxy or ethoxy group;

$R_7$ represents a phenyl that may be substituted with one or more groups $R_6$, which may be identical or different.

Among the compounds of general formula (I), an eighth subgroup of compounds is formed by the compounds for which $R_1$ represents a group $R_5$ substituted with one or more groups $R_6$ and/or $R_7$;

$R_5$ represents a phenyl;

$R_6$ represents a halogen atom, more particularly a fluorine or chlorine atom, or a group $C_{1-6}$-haloalkyl, more particularly trifluoromethyl;

$R_7$ represents a phenyl that may be substituted with one or more groups $R_6$, which may be identical or different, chosen from a halogen atom, more particularly a fluorine or chlorine atom, or a group $C_{1-6}$-alkoxy, more particularly a methoxy or ethoxy group.

Among the compounds of general formula (I), a ninth subgroup of compounds is formed by the compounds for which $R_1$ represents a group $R_5$ substituted with one or more groups $R_6$;

$R_5$ represents a 2-naphthyl group;

R$_6$ represents a group C$_{1-6}$-alkoxy, more particularly a methoxy or ethoxy group.

Among the compounds of general formula (I), a tenth subgroup of compounds is formed by the compounds for which R$_1$ represents a group R$_5$ substituted with one or more groups R$_6$;
R$_5$ represents a 1-naphthyl group;
R$_6$ represents a halogen atom, more particularly a fluorine or chlorine atom.

Among the compounds of general formula (I), an eleventh subgroup of compounds is formed by the compounds for which R$_1$ represents a group R$_5$ substituted with one or more groups R$_6$;
R$_5$ represents a 2-benzothiazolyl group;
R$_6$ represents a halogen atom, more particularly a fluorine or chlorine atom.

Among the compounds of general formula (I), a twelfth subgroup of compounds is formed by the compounds for which R$_1$ represents an unsubstituted group R$_5$;
R$_5$ represents a 7-isoquinolyl group.

Among the compounds of general formula (I), a thirteenth subgroup of compounds is formed by the compounds for which R$_1$ represents an unsubstituted group R$_5$;
R$_5$ represents a 6-isoquinolyl group.

Among the compounds of general formula (I), a fourteenth subgroup of compounds is formed by the compounds for which R$_3$ represents a hydrogen atom.

Among the compounds of general formula (I), a fifteenth subgroup of compounds is formed by the compounds for which R$_4$ represents a group chosen from a thiazolyl, a thiadiazolyl, a triazolyl, an oxazolyl and an isoxazolyl;
this group being unsubstituted or substituted with one or more groups C$_{1-6}$-alkyl, CONR$_8$R$_9$ or CON(R$_8$)(C$_{1-3}$-alkylene-NR$_{10}$R$_{11}$);
R$_8$, R$_9$, R$_{10}$ and R$_{11}$ represent, independently of each other, a hydrogen atom or a group C$_{1-6}$-alkyl. More particularly, the group C$_{1-6}$-alkyl is a methyl.

Among the compounds of general formula (I), a sixteenth subgroup of compounds is formed by the compounds for which R$_4$ represents a 4-thiazolyl group; this group being unsubstituted.

Among the compounds of general formula (I), a seventeenth subgroup of compounds is formed by the compounds for which R$_4$ represents a 2-thiazolyl group;
this group being unsubstituted or substituted with one or more groups CONR$_8$R$_9$;
R$_8$ and R$_9$ represent, independently of each other, a hydrogen atom or a group C$_{1-6}$-alkyl. More particularly, the group C$_{1-6}$-alkyl is a methyl.

Among the compounds of general formula (I), an eighteenth subgroup of compounds is formed by the compounds for which R$_4$ represents a 1,2,3-thiadiazol-4-yl group; this group being unsubstituted.

Among the compounds of general formula (I), a nineteenth subgroup of compounds is formed by the compounds for which R$_4$ represents a 1,3,4-thiadiazol-2-yl group; this group being substituted with one or more groups C$_{1-6}$-alkyl.

Among the compounds of general formula (I), a twentieth subgroup of compounds is formed by the compounds for which R$_4$ represents an isoxazol-5-yl group;
this group being substituted with one or more groups CONR$_8$R$_9$ or CON(R$_8$)(C$_{1-3}$-alkylene-NR$_{10}$R$_{11}$);
R$_8$, R$_9$, R$_{10}$ and R$_{11}$ represent, independently of each other, a hydrogen atom or a group C$_{1-6}$-alkyl. More particularly, the group C$_{1-6}$-alkyl is a methyl or ethyl.

Among the compounds of general formula (I), a twentyfirst subgroup of compounds is formed by the compounds for which R$_4$ represents a group 1H-1,2,4-triazol-5-yl; this group being substituted with one or more groups C$_{1-6}$-alkyl.

Among the compounds of general formula (I), a twentysecond subgroup of compounds is formed by the compounds for which R$_4$ represents a 2-oxazolyl group;
this group being unsubstituted or substituted with one or more groups CONR$_8$R$_9$;
R$_8$ and R$_9$ represent, independently of each other, a hydrogen atom or a group C$_{1-6}$-alkyl. More particularly, the group C$_{1-6}$-alkyl is a methyl.

Among the compounds of general formula (I), a twentythird subgroup of compounds is formed by the compounds of general formula (I) in which, simultaneously, R$_1$ and/or R$_2$ and/or R$_3$ and/or R$_4$ and/or n and/or m and/or o and/or p and/or A are as defined in the above groups.

Among the compounds of general formula (I), the following compounds may be cited (IUPAC nomenclature generated by the AutoNom software):

1. thiazol-2-ylmethyl (3aR,5s,6aS)-5-(4-chlorophenoxy)hexahydrocyclopenta[c]pyrrole-2(1H)-carboxylate (exo)
2. thiazol-2-ylmethyl (3aR,5s,6aS)-5-[4-(trifluoromethyl)phenoxy]hexahydrocyclopenta[c]pyrrole-2(1H)-carboxylate (exo)
3. thiazol-2-ylmethyl (3aR,5s,6aS)-5-[(7-ethoxy-2-naphthyl)oxy]hexahydrocyclopenta[c]pyrrole-2(1H)-carboxylate (exo)
4. thiazol-2-ylmethyl (3aR,5r,6aS)-5-[3-(trifluoromethyl)phenoxy]hexahydrocyclopenta[c]pyrrole-2(1H)-carboxylate (endo)
5. thiazol-2-ylmethyl (3aR,5s,6aS)-5-[3-(trifluoromethyl)phenoxy]hexahydrocyclopenta[c]pyrrole-2(1H)-carboxylate (exo)
6. thiazol-2-ylmethyl (3aR,5r,6aS)-5-[(4'-ethoxybiphenyl-3-yl)oxy]hexahydrocyclopenta[c]pyrrole-2(1H)-carboxylate (endo)
7. 1,2,3-thiadiazol-4-ylmethyl (3aR,5s,6aS)-5-(4-chlorophenoxy)hexahydrocyclopenta[c]pyrrole-2(1H)-carboxylate (exo)
8. (5-tert-butyl-1,3,4-thiadiazol-2-yl)methyl (3aR,5s,6aS)-5-(4-chlorophenoxy)hexahydrocyclopenta[c]pyrrole-2(1H)-carboxylate (exo)
9. 1,2,3-thiadiazol-4-ylmethyl (3aR,5s, 6aS)-5-(4-fluorophenoxy)hexahydrocyclopenta[c]pyrrole-2(1H)-carboxylate (exo)
10. (3-carbamoylisoxazol-5-yl)methyl (3aR,5s,6aS)-5-(4-fluorophenoxy)hexahydrocyclopenta[c]pyrrole-2(1H)-carboxylate (exo)
11. [3-(methylcarbamoyl)isoxazol-5-yl]methyl (3aR,5s,6aS)-5-(4-chlorophenoxy)hexahydrocyclopenta[c]pyrrole-2(1H)-carboxylate (exo)
12. (3-carbamoylisoxazol-5-yl)methyl (3aR,5s,6aS)-5-(4-chlorophenoxy)hexahydrocyclopenta[c]pyrrole-2(1H)-carboxylate (exo)
13. (1-methyl-1H-1,2,4-triazol-5-yl)methyl (3aR,5s,6aS)-5-(4-chlorophenoxy)hexahydrocyclopenta[c]pyrrole-2(1H)-carboxylate (exo)
14. (4-carbamoylthiazol-2-yl)methyl (3aR,5s,6aS)-5-(4-chlorophenoxy)hexahydrocyclopenta[c]pyrrole-2(1H)-carboxylate (exo)
15. [4-(methylcarbamoyl)thiazol-2-yl]methyl (3aR,5s,6aS)-5-(4-chlorophenoxy)hexahydrocyclopenta[c]pyrrole-2(1H)-carboxylate (exo)
16. (3-carbamoylisoxazol-5-yl)methyl (3aR,5s,6aS)-5-[3-(trifluoromethyl)phenoxy]hexahydrocyclopenta[c]pyrrole-2(1H)-carboxylate (exo)

17. [3-(methylcarbamoyl)isoxazol-5-yl]methyl (3aR,5s,6aS)-5-[3-(trifluoromethyl)phenoxy]hexahydrocyclopenta[c]pyrrole-2(1H)-carboxylate (exo)
18. thiazol-2-ylmethyl (3aR,5s,6aS)-5-[(4'-ethoxybiphenyl-3-yl)oxy]hexahydrocyclopenta[c]pyrrole-2(1H)-carboxylate (exo)
19. (4-carbamoyloxazol-2-yl)methyl (3aR,5s,6aS)-5-(4-chlorophenoxy)hexahydrocyclopenta[c]pyrrole-2(1H)-carboxylate (exo)
20. thiazol-4-ylmethyl (3aR,4S,6aS)-4-[(6-methoxy-2-naphthyl)oxy]hexahydrocyclopenta[c]pyrrole-2(1H)-carboxylate (exo)
21. thiazol-4-ylmethyl (3aR,4R,6aS)-4-[3-(trifluoromethyl)phenoxy]hexahydrocyclopenta[c]pyrrole-2(1H)-carboxylate (endo)
22. (4-carbamoylthiazol-2-yl)methyl (3aR,5s,6aS)-5-[(7-ethoxy-2-naphthyl)oxy]hexahydrocyclopenta[c]pyrrole-2(1H)-carboxylate (exo)
23. [4-(methylcarbamoyl)thiazol-2-yl]methyl (3aR,5s,6aS)-5-[(7-ethoxy-2-naphthyl)oxy]hexahydrocyclopenta[c]pyrrole-2(1H)-carboxylate (exo)
24. (3-carbamoylisoxazol-5-yl)methyl (3aR,5s,6aS)-5-[(7-ethoxy-2-naphthyl)oxy]hexahydrocyclopenta[c]pyrrole-2(1H)-carboxylate (exo)
25. [3-(methylcarbamoyl)isoxazol-5-yl]methyl (3aR,5s,6aS)-5-[(7-ethoxy-2-naphthyl)oxy]hexahydrocyclopenta[c]pyrrole-2(1H)-carboxylate (exo)
26. [4-(methylcarbamoyl)oxazol-2-yl]methyl (3aR,5s,6aS)-5-(4-chlorophenoxy)hexahydrocyclopenta[c]pyrrole-2(1H)-carboxylate (exo)
27. (3-carbamoylisoxazol-5-yl)methyl (3aR,5s,6aS)-5-[(4-chloro-1-naphthyl)oxy]hexahydrocyclopenta[c]pyrrole-2(1H)-carboxylate (exo)
28. [3-(methylcarbamoyl)isoxazol-5-yl]methyl (3aR,5s,6aS)-5-[(4-chloro-1-naphthyl)oxy]hexahydrocyclopenta[c]pyrrole-2(1H)-carboxylate (exo)
29. thiazol-4-ylmethyl (3aR,4S,6aS)-4-[(4-chloro-1-naphthyl)oxy]hexahydrocyclopenta[c]pyrrole-2(1H)-carboxylate (exo)
30. thiazol-4-ylmethyl (3aR,4R,6aS)-4-[(4'-ethoxybiphenyl-3-yl)oxy]hexahydrocyclopenta[c]pyrrole-2(1H)-carboxylate (endo)
31. (3-carbamoylisoxazol-5-yl)methyl (3aR,5s,6aS)-5-[(4'-fluorobiphenyl-4-yl)oxy]hexahydrocyclopenta[c]pyrrole-2(1H)-carboxylate (exo)
32. [3-(methylcarbamoyl)isoxazol-5-yl]methyl (3aR,5s,6aS)-5-(4-chloro-2-fluorophenoxy)hexahydrocyclopenta[c]pyrrole-2(1H)-carboxylate (exo)
33. (3-carbamoylisoxazol-5-yl)methyl (3aR,5s,6aS)-5-(4-chloro-2-fluorophenoxy)hexahydrocyclopenta[c]pyrrole-2(1H)-carboxylate (exo)
34. (3-carbamoylisoxazol-5-yl)methyl (3aR,5s,6aS)-5-(4-chloro-3-fluorophenoxy)hexahydrocyclopenta[c]pyrrole-2(1H)-carboxylate (exo)
35. [3-(methylcarbamoyl)isoxazol-5-yl]methyl (3aR,5s,6aS)-5-(4-chloro-3-fluorophenoxy)hexahydrocyclopenta[c]pyrrole-2(1H)-carboxylate (exo)
36. (3-carbamoylisoxazol-5-yl)methyl (3aR,5s,6aS)-5-(2,4-dichlorophenoxy)hexahydrocyclopenta[c]pyrrole-2(1H)-carboxylate (exo)
37. [3-(methylcarbamoyl)isoxazol-5-yl]methyl (3aR,5s,6aS)-5-(2,4-dichlorophenoxy)hexahydrocyclopenta[c]pyrrole-2(1H)-carboxylate (exo)
38. (3-carbamoylisoxazol-5-yl)methyl (3aR,5s,6aS)-5-(isoquinolin-7-yloxy)hexahydrocyclopenta[c]pyrrole-2(1H)-carboxylate (exo)
39. (3-carbamoylisoxazol-5-yl)methyl (3aR,5s,6aS)-5-(isoquinolin-6-yloxy)hexahydrocyclopenta[c]pyrrole-2(1H)-carboxylate (exo)
40. (3-carbamoylisoxazol-5-yl)methyl (3aR,5r,6aS)-5-(4-fluoro-1,3-benzothiazol-2-yl)-5-hydroxyhexahydrocyclopenta[c]pyrrole-2(1H)-carboxylate (exo)
41. (4-carbamoyloxazol-2-yl)methyl (3aR,5s,6aS)-5-[(7-ethoxy-2-naphthyl)oxy]hexahydrocyclopenta[c]pyrrole-2(1H)-carboxylate (exo)
42. (3-{[2-(dimethylamino)ethyl]carbamoyl}isoxazol-5-yl)methyl (3aR,5s,6aS)-5-(4-fluorophenoxy)hexahydrocyclopenta[c]pyrrole-2(1H)-carboxylate (exo), and its hydrochloride
43. [4-(methylcarbamoyl)oxazol-2-yl]methyl (3aR,5s,6aS)-5-[(7-ethoxy-2-naphthyl)oxy]hexahydrocyclopenta[c]pyrrole-2(1H)-carboxylate (exo)
44. (3-dimethylcarbamoylisoxazol-5-yl)methyl (3aR,5s,6aS)-5-(4-fluorophenoxy)hexahydrocyclopenta[c]pyrrole-2(1H)-carboxylate (exo)
45. (3-methylcarbamoylisoxazol-5-yl)methyl (3aR,5s,6aS)-5-[(4'-fluorobiphenyl-4-yl)oxy]hexahydrocyclopenta[c]-pyrrole-2(1H)-carboxylate (exo)

The compounds of general formula (I) may comprise one or more asymmetric carbons. They may exist in the form of enantiomers or diastereoisomers. The compounds of general formula (I) may also exist in the form of cis or trans stereoisomers. These stereoisomers, enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

In the context of the invention, the following definitions apply:

$C_{t-z}$ in which t and z may take values from 1 to 8, a carbon-based chain possibly containing from t to z carbon atoms, for example $C_{1-3}$ a carbon-based chain possibly containing from 1 to 3 carbon atoms;

alkyl, a linear or branched saturated aliphatic group; for example a group $C_{1-6}$-alkyl represents a linear or branched carbon-based chain of 1 to 6 carbon atoms, more particularly a methyl, ethyl, propyl, isopropyl, butyl, isobutyl, tert-butyl, pentyl or hexyl;

alkylene, a linear or branched saturated divalent alkyl group, for example a group $C_{1-3}$-alkylene represents a linear or branched divalent carbon-based chain of 1 to 3 carbon atoms, more particularly a methylene, ethylene, 1-methylethylene or propylene;

cycloalkyl, a cyclic alkyl group, for example a group $C_{3-7}$-cycloalkyl represents a cyclic carbon-based group of 3 to carbon atoms, more particularly a cyclopropyl, cyclobutyl, cyclopentyl, cyclohexyl or cycloheptyl;

alkoxy, a group —O-alkyl containing a linear or branched saturated aliphatic chain;

thioalkyl, a group —S-alkyl containing a linear or branched saturated aliphatic chain;

haloalkyl, an alkyl group in which one or more hydrogen atoms have been replaced with a halogen atom;

haloalkoxy, an alkoxy group in which one or more hydrogen atoms have been replaced with a halogen atom;

halothioalkyl, a thioalkyl group in which one or more hydrogen atoms have been replaced with a halogen atom;

halogen atom, a fluorine, a chlorine, a bromine or an iodine;

The term 'exo' corresponds to the group -A-R1 in the cis position relative to the ring junction hydrogens. The term 'endo' corresponds to the group -A-R1 in the trans position relative to the ring junction hydrogens;

r and s indicate the stereochemistry of the pseudo-asymmetric carbon atoms, according to the IUPAC rules.

The compounds of the invention may be prepared according to various methods, illustrated by the schemes that follow. These methods, and also the intermediate compounds used, are subjects of the present invention.

Scheme 1

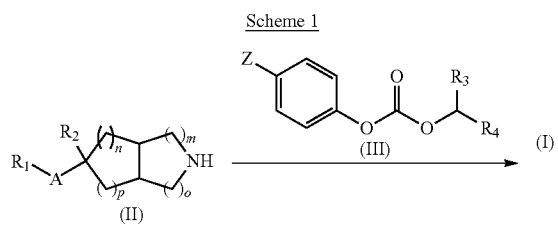

Thus, a first preparation method (Scheme 1) consists in reacting an amine of general formula (II), in which A, $R_1$, $R_2$, m, n, o and p are as defined in the general formula (I) defined above, with a carbonate of general formula (III) in which Z represents a hydrogen atom or a nitro group, $R_3$ and $R_4$ are as defined in the general formula (I) defined above, in the presence of a base such as triethylamine, pyridine, N,N-dimethylaminopyridine or N,N-diisopropylethylamine, in a solvent such as toluene, acetonitrile or dichloroethane, at a temperature between room temperature and the reflux temperature of the solvent.

loxycarbonyl), a Cbz (benzyloxycarbonyl), a benzyl or a benzhydryl;

either with an alcohol derivative of general formula $R_1OH$ (IV), in which $R_1$ is as defined above, using the Mitsunobu reaction conditions (*Synthesis*, 1981, 1-28), or with a halo derivative of general formula $R_1X$ (IVa), in which $R_1$ is as defined above and X represents a fluorine, chlorine, bromine or iodine atom, using the aromatic or heteroaromatic nucleophilic substitution or Buchwald O-arylation or O-heteroarylation reactions, for example using a palladium or copper catalyst;

followed by a deprotection reaction, for example in the presence of trifluoroacetic acid or of a solution of hydrogen chloride in isopropanol or dioxane, to give the amine of general formula (IIb) in which G, $R_2$, m, n, o and p are as defined in the general formula (IIa) defined above and $R_1$ is as defined above. The derivative of general formula (IIb) thus obtained is then converted into a compound of general formula (I) according to a condensation reaction with a carbonate of general formula (III) as defined above, under the conditions described above (Scheme 1).

One variant for obtaining the compounds of general formula (I) (Scheme 2), in which A more particularly represents an oxygen atom or a group —O—$C_{1-6}$-alkylene-, consists in deprotecting an alcohol of general formula (IIa) as defined above), according to a deprotection reaction as defined above, so as to obtain an amino alcohol of general formula (IIc), and then in reacting this amino alcohol of general formula (IIc) in which G, $R_2$, m, n, o and p are as defined in the general formula (IIa) defined above, with a carbonate of general formula (III) as defined above, under the conditions described above (Scheme 1), to give the carbamate derivative of general formula (Ia), in which G, $R_2$, $R_3$, $R_4$, m, n, o and p are as Scheme 2

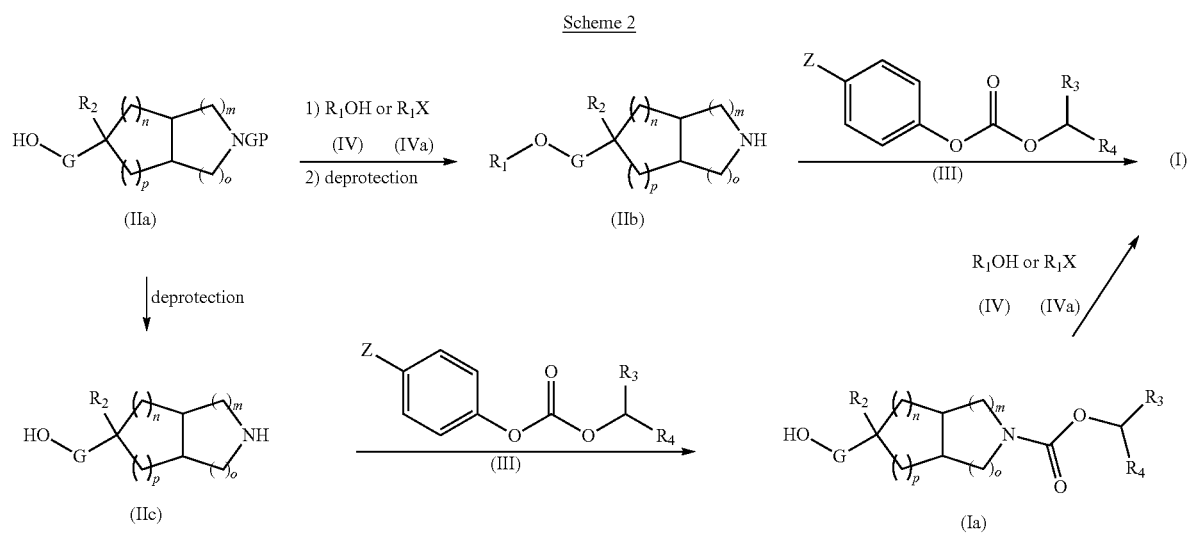

A second method (Scheme 2) for obtaining the compounds of general formula (I) in which A more particularly represents an oxygen atom or a group —O—$C_{1-6}$-alkylene-consists in reacting, in a first stage, an alcohol of general formula (IIa), in which $R_2$, m, n, o and p are as defined in the general formula (I) defined above, G represents a part of the group A as defined in the general formula (I), namely either a covalent bond or the $C_{1-6}$-alkylene-part of the group —O—$C_{1-6}$-alkylene-, and PG represents a protecting group such as a Boc (tert-butyloxycarbonyl), a Cbz (benzyloxycarbonyl), a benzyl or a benzhydryl);

defined in the general formula (IIa) defined above. The carbamate derivative (Ia) thus obtained is then converted into a compound of general formula (I) via the action of an alcohol of general formula $R_1OH$ (IV) as defined above, using the Mitsunobu reaction conditions or via the action of a halo derivative of general formula $R_1X$ (IVa) as defined above using aromatic or heteroaromatic nucleophilic substitution or Buchwald O-arylation or O-heteroarylation reactions, for example using a palladium or copper catalyst.

Scheme 3

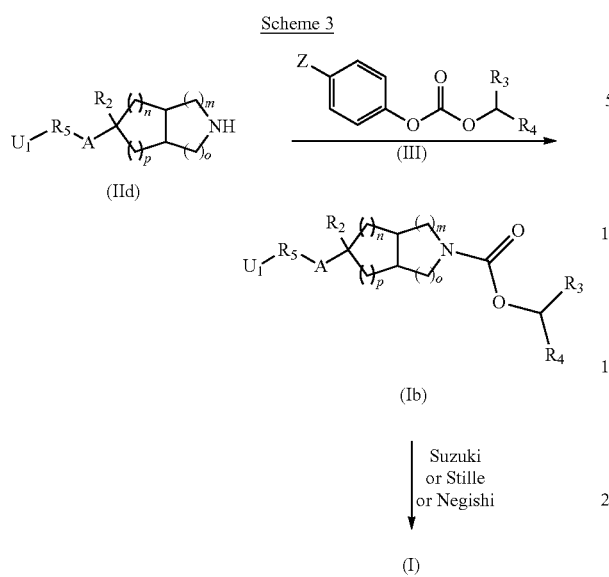

A third method (Scheme 3) was developed for the synthesis of the compounds of general formula (I), in which $R_1$ represents a group $R_5$ substituted especially with a group $R_6$ of the type $C_{1-6}$-alkyl, $C_{3-7}$-cycloalkyl or $C_{3-7}$-cycloalkyl-$C_{1-3}$-alkylene, or with a group $R_7$ as defined in the general formula (I) defined above. Thus, the first step consists in reacting an amine of general formula (IId), in which A, $R_2$, $R_5$, m, n, o and p are as defined in the general formula (I) defined above and $U_1$ represents a chlorine, bromine or iodine atom or a triflate group, with a carbonate of general formula (III) as defined above, under the conditions described above (Scheme 1), to give the carbamate derivative of general formula (Ib), in which A, $R_2$, $R_3$, $R_4$, $R_5$, m, n, o and p are as defined in the general formula (I) defined above and $U_1$ is as defined above. The coupling reaction catalysed with a transition metal such as palladium(0) is then performed on the key intermediate of general formula (Ib) as defined above, $U_1$ being in the position in which it is desired to introduce the group $R_6$ or $R_7$ (Scheme 3):

either via a reaction of Suzuki type, for example using an alkyl, cycloalkyl, aryl or heteroaryl boronic acid,
or according to a reaction of Stille type, for example using an aryl or heteroaryl tri-alkylstannous derivative,
or via a reaction of Negishi type, for example using an alkyl, cycloalkyl, aryl or heteroaryl halide zincate derivative.

Another subject of the present invention relates to the compounds of general formula (Ia)

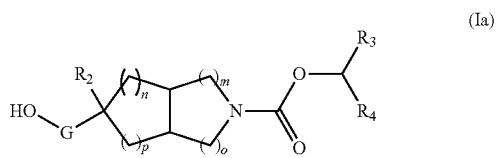

in which $R_2$, $R_3$, $R_4$, m, n, o and p are as defined in the general formula (I), and G represents part of the group A as defined in the general formula (I), namely either a covalent bond or the $C_{1-6}$-alkylene part of the group —O—$C_{1-6}$-alkylene.

Among these compounds, mention may be made of:
[3-(ethoxycarbonyl)isoxazol-5-yl]methyl (3aR,5r,6aS)-5-hydroxyhexahydrocyclopenta[c]pyrrole-2(1H)-carboxylate;
thiazol-2-ylmethyl (3aR,5r,6aS)-5-hydroxyhexahydrocyclopenta[c]pyrrole-2(1H)-carboxylate.

Another subject of the present invention relates to the compounds of general formula (II):

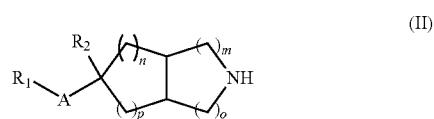

in which $R_1$, $R_2$, m, n, o and p are as defined in the general formula (I), A represents an oxygen atom or a covalent bond, given that when A represents a covalent bond, then $R_1$ represents a benzothiazolyl group.

Among these compounds, mention may be made of:
(3aR,5s,6aS)-5-[3-(trifluoromethyl)phenoxy]octahydrocyclopenta[c]pyrrole;
(3aR,5s,6aS)-5-(4-fluorophenoxy)octahydrocyclopenta[c]-pyrrole (1H NMR 400 MHz DMSO, δ (ppm): 7.10 (t, 2H); 6.95 (m, 2H); 4.85 (m, 1H); 2.90 (m, 2H); 2.75 (m, 4H); 2.00 (m, 2H); 1.70 (m, 2H));
(3aR,5r,6aS)-5-(4-fluoro-1,3-benzothiazol-2-yl)octahydrocyclopenta[c]pyrrol-5-ole;
(3aR,5s,6aS)-5-(4-Chloro-3-fluorophenoxy)octahydrocyclopenta[c]pyrrole;
(3aR,5s,6aS)-5-(4-chlorophenoxy)octahydrocyclopenta[c]-pyrrole;
(3aR,5s,6aS)-5-[(7-ethoxy-2-naphthyl)oxy]octahydrocyclopenta[c]pyrrole;
(3aR,5r,6aS)-5-[(4'-ethoxybiphenyl-3-yl)oxy]octahydrocyclopenta[c]pyrrole;
(3aR,5s,6aS)-5-[(4'-ethoxybiphenyl-3-yl)oxy]octahydrocyclopenta[c]pyrrole;
(3aR,4S,6aS)-4-[(4-chloro-1-naphthyl)oxy]octahydrocyclopenta[c]pyrrole;
(3aR,4R,6aS)-4-[(4'-ethoxybiphenyl-3-yl)oxy]octahydrocyclopenta[c]pyrrole.

Another subject of the present invention relates to the compounds of general formula (IIe):

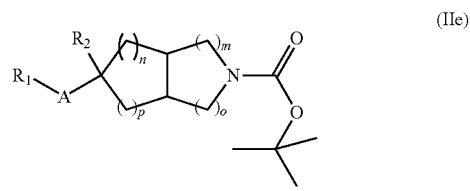

in which $R_1$, $R_2$, m, n, o and p are as defined in the general formula (I), A represents an oxygen atom or a covalent bond, given that when A represents a covalent bond, then R1 represents a benzothiazolyl group.

Among these compounds, mention may be made of:
tert-butyl (3aR,5r,6aS)-5-[(4'-ethoxybiphenyl-3-yl)oxy]hexahydrocyclopenta[c]pyrrole-2(1H)-carboxylate;
(3aR,5s,6aS)-5-(3-bromophenoxy) tert-butyl hexahydrocyclopenta[c]pyrrole-2(1H)-carboxylate;
tert-butyl (3aR,5s,6aS)-5-[(4'-ethoxybiphenyl-3-yl)oxy]hexahydrocyclopenta[c]pyrrole-2(1H)-carboxylate;

tert-butyl (3aR,4S,6aS)-4-[(4-chloro-1-naphthyl)oxy] hexahydrocyclopenta[c]pyrrole-2(1H)-carboxylate;
tert-butyl (3aR,4R,6aS)-4-(3-bromophenoxy)hexahydrocyclopenta[c]pyrrole-2(1H)-carboxylate;
tert-butyl (3aR,4R,6aS)-4-[(4'-ethoxybiphenyl-3-yl)oxy] hexahydrocyclopenta[c]pyrrole-2(1H)-carboxylate;
tert-butyl (3aR,5r,6aS)-5-(4-fluoro-1,3-benzothiazol-2-yl)-5-hydroxyhexahydrocyclopenta[c]pyrrole-2(1H)-carboxylate.

The other compounds of general formulae (II), (IIa), (IIb), (IIc), (IId), (III), (IV) and (IVa) and also the other reagents are commercially available or described in the literature, or alternatively may be prepared according to methods that are described therein or that are known to those skilled in the art.

The examples that follow illustrate the preparation of a few compounds of the invention. These examples are not limiting, and serve merely to illustrate the invention. The microanalyses, IR and NMR spectra and/or the LC-MS (liquid chromatography coupled to mass spectroscopy) spectra confirm the structures and impurities of the compounds obtained.

m.p. (° C.) represents the melting point in degrees Celsius.

$R_f$ indicates the retention time obtained by TLC (thin-layer chromatography) analysis.

The numbers indicated in parentheses in the example titles correspond to those in the first column of the tables hereinbelow.

The IUPAC (International Union of Pure and Applied Chemists) nomenclature has been used for the naming of the compounds in the examples below.

EXAMPLE 1

Compound 6 thiazol-2-ylmethyl (3aR,5r,6aS)-5-[(4'-ethoxybiphenyl-3-yl)-oxy]hexahydrocyclopenta[c]pyrrole-2(1H)-carboxylate (endo)

1.1. tert-butyl (3aR,5s,6aS)-5-(3-bromophenoxy) hexahydrocyclopenta[c]pyrrole-2(1H)-carboxylate 0.20 g (0.88 mmol) of tert-butyl (3aR,5r,6aS)-5-hydroxyhexahydrocyclopenta[c]pyrrole-2(1H)-carboxylate (obtained according to a process described in WO 2006/108 059) is dissolved in 4.4 mL of dimethylformamide, and 0.19 g (1.10 mmol) of 1-bromo-3-iodobenzene and 0.03 g (1.32 mmol) of sodium hydride are then added. The mixture is stirred at 90° C. for 15 hours. The resulting mixture is diluted by adding water and ethyl acetate. This mixture is extracted with ethyl acetate and the combined organic phases are then dried over sodium sulfate and evaporated to dryness after filtration. The residue is purified by chromatography on silica gel, eluting with a mixture of cyclohexane and ethyl acetate. 0.175 g (52%) of expected product is obtained in the form of a colourless oil.

1.2. tert-butyl (3aR,5r,6aS)-5-[(4'-ethoxybiphenyl-3-yl)oxy]hexahydrocyclopenta[c]pyrrole-2(1H)-carboxylate Under an inert atmosphere, 0.170 g (0.44 mmol) of tert-butyl (3aR,5s,6aS)-5-(3-bromophenoxy)hexahydrocyclopenta[c]-pyrrole-2(1H)-carboxylate, obtained in step 1.1., 0.088 g (0.53 mmol) of 4-ethoxyphenylboronic acid and 0.434 g (1.33 mmol) of caesium carbonate are introduced into 5 ml of a 9/1 mixture of tetrahydrofuran and water. 0.036 g (0.04 mmol) of PdCl₂dppf.CH₂Cl₂ is added and the medium is heated at 75° C. for 15 hours. The medium is allowed to cool to room temperature and then diluted with ethyl acetate and water. The organic phase is separated out and extracted twice with ethyl acetate, and the combined organic phases are washed with saturated aqueous sodium chloride solution and dried over sodium sulfate. After evaporating off the solvent, the residue is purified by chromatography on silica gel, eluting with a mixture of cyclohexane and ethyl acetate. 0.145 g (77%) of expected product is obtained in the form of an oil.

LC-MS: M+H=424

1.3. (3aR,5r,6aS)-5-[(4'-ethoxybiphenyl-3-yl)oxy] octahydrocyclopenta[c]pyrrole 0.14 g (0.34 mmol) of tert-butyl (3aR,5r,6aS)-5-[(4'-ethoxybiphenyl-3-yl)oxy]hexahydrocyclopenta[c]pyrrole-2 (1H)-carboxylate, obtained in step 1.2., is dissolved in dichloromethane, and 1.71 mL (6.85 mmol) of a 4N solution of hydrogen chloride in dioxane are then added. The mixture is stirred at room temperature for 2 hours.

Work-up with 1M sodium hydroxide after extraction with dichloromethane and then drying over sodium sulfate and evaporation to dryness gives 0.084 g of a colourless oil.

1.4. thiazol-2-ylmethyl (3aR,5r,6aS)-5-[(4'-ethoxybiphenyl-3-yl)oxy]hexahydrocyclopenta[c]pyrrole-2 (1H)-carboxylate 0.07 g (0.28 mmol) of (3aR,5r,6aS)-5-[(4'-ethoxybiphenyl-3-yl)oxy]octahydrocyclopenta[c]pyrrole, obtained in step 1.3., is dissolved in 2.5 mL of dichloromethane and 0.06 mL (0.34 mmol) of N,N-diisopropylethylamine and 0.09 (0.31 mmol) of thiazol-4-ylmethyl (4-nitrophenyl)carbonate (WO 2008/013 834) is then added. The mixture is stirred at room temperature for 15 hours and then diluted with ethyl acetate. The organic phase is washed successively with aqueous 1M sodium hydroxide solution and then twice with saturated aqueous sodium chloride solution, dried over sodium sulfate, filtered and evaporated to dryness. The residue obtained is purified by chromatography on silica gel, eluting with a mixture of cyclohexane and ethyl acetate. 0.088 g (67%) of expected product is obtained in the form of a yellow oil.

LC-MS: M+H=465

¹H NMR (DMSO) δ (ppm): 7.80 (d, 1H); 7.70 (d, 1H); 7.60 (d, 2H); 7.30 (t, 1H); 7.15 (d, 1H); 7.05 (s, 1H); 7.00 (d, 2H); 6.80 (d, 1H); 5.35 (S, 2H); 5.00 (m, 1H); 4.10 (q, 2H); 3.55 (m, 2H); 3.35 (m, 2H); 2.75 (m, 2H); 2.30 (m, 2H); 1.70 (m, 2H); 1.35 (t, 3H).

EXAMPLE 2

Compound 7

1,2,3-thiadiazol-4-ylmethyl (3aR,5s,6aS)-5-(4-chlorophen-oxy)hexahydrocyclopenta[c]pyrrole-2(1H)-carboxylate (exo)

2.1. (3aR,5s,6aS)-5-(4-chlorophenoxy)octahydrocyclopenta-[c]pyrrole 2.00 g (8.80 mmol) of tert-butyl (3aR,5r,6aS)-5-hydroxyhexahydrocyclopenta[c]pyrrole-2(1H)-carboxylate (see synthesis: WO 2006/108 059) are dissolved in 88 mL of toluene. 2.77 g (10.56 mmol) of triphenylphosphine and 1.47 g (11.44 mmol) of 4-chlorophenol are added, and then the medium is cooled to 0° C., followed by slow addition of a solution of 1.69 g (9.68 mmol) of diethyl azodicarboxylate in 10 mL of toluene. The medium is stirred for 14 hours at room temperature. The resulting mixture is concentrated under reduced pressure. The residue obtained is taken up in aqueous 1N sodium hydroxide solution and extracted twice with dichloromethane. The combined organic phases are washed once with saturated aqueous sodium chloride solution, dried over sodium sulfate, filtered and concentrated under vacuum. The residue obtained is taken up in 50 mL of dichloromethane, followed by deprotection by slow addition of 50 mL of a 4N solution of hydrogen chloride in dioxane. After stirring for 1 hour at room temperature, the medium is concentrated under vacuum and the residue is taken up in aqueous 1N hydrochloric acid solution. The aqueous phase is extracted twice with ethyl acetate and then slowly basified to pH 10 by addition of potassium carbonate. The aqueous phase is extracted three times with dichloromethane. These three organic extracts are combined, washed once with saturated aqueous sodium chloride solution, dried over sodium sulfate, filtered and concentrated under vacuum. The residue is purified by chromatography on silica gel, eluting with a 98/2/0.2 to 95/5/0.5 mixture of dichloromethane, methanol and 30% aqueous ammonia. 1.22 g (61%) of expected product are obtained in the form of a wax.

LC-MS: M+H=238
$^1$H NMR (DMSO) δ (ppm): 7.35 (d, 2H); 7.00 (d, 2H); 4.95 (m, 1H); 3.55 (broad s, 1H); 2.80 (m, 2H); 2.75-2.60 (m, 4H); 2.00 (m, 2H); 1.70 (m, 2H).

2.2. 1,2,3-thiadiazol-4-ylmethyl (3aR,5S,6aS)-5-(4-chloro-phenoxy)hexahydrocyclopenta[c]pyrrole-2 (1H)-carboxylate 0.070 g (0.61 mmol) of 1,2,3-thiadiazole-4-methanol (DD232495) and 0.18 mL (1.06 mmol) of N,N-diisopropylethylamine are dissolved in 1 mL of 1,2-dichloroethane and then cooled to 0° C. 0.11 g (0.56 mmol) of p-nitrophenyl chloroformate dissolved in 2 mL of 1,2-dichloroethane is added. The mixture is stirred at room temperature for 15 minutes and a solution of 0.12 g (0.50 mmol) of (3aR,5s,6aS)-5-(4-chlorophenoxy)octahydrocyclopenta[c]pyrrole, obtained in step 2.1., is then added. The mixture is heated at 60° C. for 15 hours.

After cooling to room temperature, aqueous 1N sodium hydroxide solution is added, and the product is extracted with dichloromethane. The combined organic phases are then washed successively with saturated aqueous ammonium chloride solution, and then with saturated aqueous sodium chloride solution. After drying the organic phases over sodium sulfate, they are filtered and evaporated to dryness. After purifying on a column of silica gel, eluting with a 99/1/0.1 mixture of dichloromethane, methanol and 30% aqueous ammonia, 0.068 g (58%) of expected product is obtained in the form of a white powder.

Melting point (° C.): 122-124° C.
LC-MS: M+H=380
$^1$H NMR (DMSO) δ (ppm): 9.20 (s, 1H); 7.30 (d, 2H); 6.90 (d, 2H); 5.55 (s, 2H); 4.95 (m, 1H); 3.55 (m, 2H); 3.20 (m, 2H); 2.80 (m, 2H); 2.05-1.90 (m, 2H); 1.90-1.80 (m, 2H).

EXAMPLE 3

Compound 8

(5-tert-butyl-1,3,4-thiadiazol-2-yl)methyl (3aR,5s,6aS)-5-(4-chlorophenoxy)hexahydrocyclopenta[c] pyrrole-2(1H)-carboxylate (exo)

3.1 (5-tert-butyl-[1,3,4]thiadiazol-2-yl)methanol 1 g (4.67 mmol) of ethyl 5-tert-butyl-1,3,4-thiadiazole-2-carboxylate is dissolved in 45 mL of methanol and 0.353 g (9.33 mmol) of sodium borohydride is added portionwise, with stirring, at room temperature. The medium is stirred for 1 hour at room temperature and then concentrated under vacuum. The residue obtained is taken up in aqueous solution saturated with sodium chloride. The aqueous solution is brought to ph 7 by slowly adding, with stirring, aqueous 1N hydrochloric acid solution. After stirring for 1 hour at room temperature, the aqueous phase is extracted three times with dichloromethane and the combined organic phases are then washed once with saturated aqueous sodium chloride solution, dried over sodium sulfate, filtered and concentrated to dryness. 0.802 g (100%) of the expected product is obtained in the form of an oil.

LC-MS: M+H=173
$^1$H NMR (CDCl$_3$) δ (ppm): 5.10 (d, 2H); 4.60 (t, 1H); 1.65 (s, 9H).

3.2. (5-tert-butyl-1,3,4-thiadiazol-2-yl)methyl (3aR, 5s,6aS)-5-(4-chlorophenoxy)hexahydrocyclopenta [c]-pyrrole-2(1H)-carboxylate The process is performed according to the procedure described in Example 2, step 2.2. Starting with 0.10 g (0.42 mmol) of (3aR,5s,6aS)-5-(4-chlorophenoxy)octahydrocyclopenta[c]pyrrole, obtained in step 2.1., 0.07 g (0.46 mmol) of (5-tert-butyl-[1,3,4]thiadiazol-2-yl)methanol, obtained in step 3.1., 0.08 g (0.42 mmol) of para-nitrophenyl chloroformate and 0.15 mL (0.88 mmol) of N,N-diisopropylethylamine, and after chromatography on preparative silica gel plates, eluting with a 98/2/0.2 mixture of dichloromethane, methanol and 30% aqueous ammonia, 0.08 g (54%) of expected product is obtained in the form of a wax.

LC-MS: M+H=436
$^1$H NMR (DMSO) δ (ppm): 7.30 (d, 2H); 6.90 (d, 2H); 5.4 (s, 2H); 4.95 (m, 1H); 3.55 (m, 2H); 3.25 (m, 2H); 2.85 (m, 2H); 2.00 (m, 2H); 1.90 (m, 2H); 1.45 (s, 9H).

EXAMPLE 4

Compound 16

(3-carbamoylisoxazol-5-yl)methyl (3aR,5s,6aS)-5-[3-(trifluoromethyl)phenoxy]hexahydrocyclopenta [c]pyrrole-2(1H)-carboxylate (exo)

4.1. (3aR,5s,6aS)-5-[3-(trifluoromethyl)phenoxy] octahydrocyclopenta[c]pyrrole

The process is performed according to the procedure described in Example 2, step 2.1. Starting with 1.4 g (6.16 mmol) of tert-butyl (3aR,5r,6aS)-5-hydroxyhexahydrocyclopenta[c]pyrrole-2(1H)-carboxylate (see synthesis: WO 2006/108 059), 1.39 g (8.62 mmol) of 3-trifluoromethyl-phenol, 1.39 g (8.01 mmol) of diethyl azodicarboxylate, 2.26 g (8.62 mmol) of triphenylphosphine and 30 mL of a 4N solution of hydrogen chloride in dioxane, 0.48 g (29%) of expected product is obtained in the form of a wax.

LC-MS: M+H=272

$^1$H NMR (CDCl$_3$) δ (ppm): 7.45 (t, 1H); 7.30-7.05 (m, 3H); 4.95 (tq, 1H); 3.05-2.70 (m, 6H); 2.25 (m, 2H); 1.65 (m, 2H).

4.2. 3-carbamoylisoxazol-5-ylmethyl 4-nitrophenyl carbonate

To a solution of 2.0 g (14.07 mmol) of 3-carbamoylisoxazol-5-ylmethanol, 1.71 ml (21.11 mmol) of pyridine and 0.17 g (1.41 mmol) of N,N-dimethylaminopyridine in 15 mL of dichloromethane, cooled to about 0° C., are added portionwise 2.84 g (14.07 mmol) of 4-nitrophenyl chloroformate. The medium is kept stirring at 0° C. for 1 hour and then at room temperature for 1 hour.

The precipitate formed is filtered off and then rinsed thoroughly with diisopropyl ether. After drying under vacuum at about 60° C., 3.12 g (72%) of expected product are obtained in the form of a white solid, which is used without further purification in the following step.

m.p. (° C.): 143-145° C.

$^1$H NMR (DMSO) δ (ppm): 8.40 (d, 2H); 8.25 (broad s, 1H); 7.90 (broad s, 1H); 7.65 (d, 2H); 7.0 (s, 1H); 5.50 (s, 2H).

4.3. (3-carbamoylisoxazol-5-yl)methyl (3aR,5s,6aS)-5-[3-(trifluoromethyl)phenoxy]hexahydrocyclopenta[c]pyrrole-2(1H)-carboxylate The process is performed according to the procedure described in Example 1, step 1.3. Starting with 0.15 g of (3aR,5s,6aS)-5-[3-(trifluoromethyl)phenoxy]octahydrocyclopenta[c]pyrrole, obtained in step 4.1., 0.18 g (0.61 mmol) of 3-carbamoylisoxazol-5-ylmethyl 4-nitrophenyl carbonate, obtained in step 4.2., 0.03 g (0.28 mmol) of N,N-dimethylaminopyridine and 0.21 mL (1.22 mmol) of N,N-diisopropylethylamine, and after chromatography on silica gel, eluting with a mixture from 99/1/0.1 to 97/3/0.3 of dichloromethane, methanol and 30% aqueous ammonia, 0.21 g (87%) of expected product is obtained in the form of a white powder.

Melting point (° C.): 130-132° C.

LC-MS: M+H=440

$^1$H NMR (DMSO) δ (ppm): 8.15 (s, 1H); 7.85 (s, 1H); 7.55 (t, 1H); 7.25 (d, 1H); 7.20 (d, 1H); 7.15 (s, 1H); 6.80 (s, 1H); 5.25 (s, 2H); 5.10 (m, 1H); 3.55 (m, 2H); 3.20 (m, 2H); 2.85 (m, 2H); 2.05-1.95 (m, 2H); 1.95-1.80 (m, 2H).

EXAMPLE 5

Compound 22

(4-carbamoylthiazol-2-yl)methyl (3aR,5s,6aS)-5-[(7-ethoxy-2-naphthyl)oxy]hexahydrocyclopenta[c]pyrrole-2(1H)-carboxylate (exo)

5.1. (3aR,5s,6aS)-5-[(7-ethoxy-2-naphthyl)oxy]octahydrocyclopenta[c]pyrrole The process is performed according to the procedure described in Example 2, step 2.1. Starting with 1.4 g (6.16 mmol) of tert-butyl (3aR,5r,6aS)-5-hydroxyhexahydrocyclopenta[c]pyrrole-2(1H)-carboxylate (see synthesis: WO 2006/108 059), 1.51 g (8.00 mmol) of 7-ethoxy-2-naphthol, 1.28 g (7.39 mmol) of diethyl azodicarboxylate and 1.93 g (7.39 mmol) of triphenylphosphine, and 30 mL of a 4N solution of hydrogen chloride in dioxane, 1.36 g (74%) of expected product are obtained in the form of an oil.

LC-MS: M+H=298

$^1$H NMR (DMSO) δ (ppm): 7.70 (d, 2H); 7.20 (m, 2H), 7.00 (m, 2H), 5.05 (m, 1H); 4.15 (dq, 2H); 2.95 (m, 2H); 2.85-2.50 (m, 4H); 2.10 (m, 2H); 1.85 (m, 2H); 1.40 (t, 3H).

5.2. methyl 2-hydroxymethylthiazole-4-carboxylate

5.2.1. ethyl 2-[(acetyloxy)methyl]thiazole-4-carboxylate 2.7 g (10.80 mmol) of ethyl 2-(bromomethyl)thiazole-4-carboxylate are dissolved in 108 mL of acetonitrile. 2.225 g (22.67 mmol) of potassium acetate are added and the medium is stirred at room temperature for 14 hours.

The resulting mixture is concentrated under reduced pressure. The residue obtained is taken up in aqueous sodium chloride solution and extracted twice with dichloromethane. The combined organic phases are dried over sodium sulfate, filtered and concentrated to dryness. 2.347 g (95%) of expected product are obtained in the form of a wax.

$^1$H NMR (CDCl$_3$) δ (ppm): 8.15 (s, 1H); 5.35 (s, 2H); 4.35 (dq, 2H); 2.10 (s, 3H); 1.35 (t, 3H).

5.2.2. methyl 2-hydroxymethylthiazole-4-carboxylate 2.347 g (10.24 mmol) of ethyl 2-acetoxymethylthiazole-4-carboxylate, obtained in step 5.2.1., are dissolved in 100 mL of a 5/1 mixture of dichloromethane and methanol. 2.58 mL (11.26 mmol) of a 4.37N solution of sodium methoxide in methanol are added and the medium is stirred at room temperature for two hours and then concentrated under reduced pressure. The residue obtained is taken up in saturated aqueous sodium chloride solution and extracted three times with dichloromethane. The combined organic phases are washed once with saturated aqueous sodium chloride solution, dried over sodium sulfate, filtered and concentrated to dryness. The residue obtained is purified by chromatography on silica gel, eluting with a 98/2/0.2 mixture of dichloromethane, methanol and 30% aqueous ammonia. 0.92 g of expected product is obtained in the form of a white powder.

Melting point (° C.): 158-160° C.

$^1$H NMR (CDCl$_3$) δ (ppm): 8.10 (s, 1H); 4.95 (s, 2H); 3.90 (s, 3H); 2.50 (broad s, 1H).

5.3. [4-(methoxycarbonyl)thiazol-2-yl]methyl (3aR,5s,6aS)-5-[(7-ethoxy-2-naphthyl)oxy]hexahydrocyclopenta[c]pyrrole-2(1H)-carboxylate The process is performed according to the procedure described in Example 2, step 2.2. Starting with 0.25 g (0.84 mmol) of (3aR,5s,6aS)-5-[(7-ethoxy-2-naphthyl)oxy]-octahydrocyclopenta[c]pyrrole, obtained in step 5.1., 0.18 g (1.09 mmol) of methyl 2-hydroxymethylthiazole-4-carboxylate, obtained in step 5.2., 0.20 g (1.01 mmol) of para-nitrophenyl chloroformate and 0.37 mL (2.10 mmol) of N,N-diisopropylethylamine, and after chromatography on silica gel, eluting with a 99/1/0.1 mixture of dichloromethane, methanol and aqueous ammonia, 0.25 g of expected product is obtained in the form of a wax.

5.4. (4-carbamoylthiazol-2-yl)methyl (3aR,5s,6aS)-5-[(7-ethoxy-2-naphthyl)oxy]hexahydrocyclopenta[c]pyrrole-2(1H)-carboxylate In a sealed tube, 0.125 g (0.25 mmol) of [4-(methoxycarbonyl)thiazol-2-yl]methyl (3aR,5s,6aS)-5-[(7-ethoxy-2- naphthyl)oxy]hexahydrocyclopenta[c]pyrrole-2(1H)-carboxylate, obtained in step 5.3., is dissolved in 5 mL of methanol. 10 mL (70 mmol) of a 7N solution of ammonia in methanol are added and the medium, in a sealed tube, is heated at 60° C. for 14 hours with stirring.

The medium cooled to room temperature is concentrated under vacuum and the residue obtained is chromatographed on preparative plates of silica gel, eluting with a 95/5/0.5 mixture of dichloromethane, methanol and 30% aqueous ammonia. 0.072 g (59%) of the expected product is thus obtained in the form of a white powder.

Melting point (° C.): 143-145° C.

LC-MS: M+H=482

$^1$H NMR (DMSO) δ (ppm): 8.30 (s, 1H); 7.75 (d, 2H); 7.75 (s, 1H); 7.60 (s, 1H); 7.20 (m, 2H); 6.95 (m, 2H); 5.40 (s, 2H); 5.10 (m, 1H); 4.15 (dq, 2H); 3.60 (m, 2H); 3.25 (m, 2H); 2.90 (m, 2H); 2.15-2.05 (m, 2H); 2.05-1.90 (m, 2H); 1.40 (t, 3H).

EXAMPLE 6

Compound 25

[3-(methylcarbamoyl)isoxazol-5-yl]methyl (3aR,5s,6aS)-5-[(7-ethoxy-2-naphthyl)oxy]hexahydrocyclopenta[c]pyrrole-2(1H)-carboxylate (exo)

6.1. 3-methylcarbamoylisoxazol-5-ylmethyl 4-nitrophenyl carbonate

The process is performed according to the procedure described in Example 4 (step 4.2.). Starting with 2.00 g (12.81 mmol) of 3-methylcarbamoylisoxazol-5-ylmethanol, 2.58 g (12.81 mmol) of 4-nitrophenyl chloroformate, 1.52 g (19.21 mmol) of pyridine and 0.157 g (1.28 mmol) of N,N-dimethylaminopyridine, 2.6 g (63%) of pure product are obtained in the form of a white powder.

m.p. (° C.): 166-168° C.

$^1$H NMR (CDCl$_3$) δ (ppm): 8.40 (d, 2H); 7.50 (d, 2H); 7.0 (s, 1H); 6.90 (broad s, 1H); 5.50 (s, 2H); 3.10 (d, 3H).

6.2. [3-(methylcarbamoyl)isoxazol-5-yl]methyl (3aR,5s,6aS)-5-[(7-ethoxy-2-naphthyl)oxy]hexahydrocyclopenta[c]pyrrole-2(1H)-carboxylate The process is performed according to the procedure described in Example 1, step 1.3. Starting with 0.15 g (0.50 mmol) of (3aR,5s,6aS)-5-[(7-ethoxy-2-naphthyl)oxy]-octahydrocyclopenta[c]pyrrole, obtained in step 5.1., 0.17 g (0.55 mmol) of 3-methylcarbamoylisoxazol-5-ylmethyl 4-nitrophenyl carbonate, obtained in step 6.1., 0.03 g (0.28 mmol) of N,N-dimethylaminopyridine and 0.19 mL (1.11 mmol) of N,N-diisopropylethylamine, and after chromatography on silica gel, eluting with a 98/2/0.2 mixture of dichloromethane, methanol and aqueous ammonia, 0.13 g (54%) of expected product is obtained in the form of a white powder.

Melting point (° C.) 108-110° C.

LC-MS: M+H=480

$^1$H NMR (DMSO) δ (ppm): 8.69 (s, 1H); 7.69 (d, 2H); 7.18 (s, 1H); 7.16 (s, 1H); 6.95 (m, 2H); 6.81 (s, 1H); 5.25 (s, 2H); 5.06 (m, 1H); 4.12 (dq, 2H); 3.56 (m, 2H); 3.23 (m, 2H); 2.85 (m, 2H); 2.77 (d, 3H); 2.06 (m, 2H); 1.94 (m, 2H); 1.38 (t, 3H).

EXAMPLE 7

Compound 26

[4-(methylcarbamoyl)oxazol-2-yl]methyl (3aR,5s,6aS)-5-(4-chlorophenoxy)hexahydrocyclopenta[c]pyrrole-2(1H)-carboxylate (exo)

7.1 methyl 2-hydroxymethyloxazole-4-carboxylate

7.1.1. ethyl 2-[(acetyloxy)methyl]oxazole-4-carboxylate 9.5 g (10.80 mmol) of ethyl 2-(bromomethyl)oxazole-4-carboxylate are dissolved in 135 mL of acetonitrile. 9.96 g (101.47 mmol) of potassium acetate are added and the medium is stirred at room temperature for 14 hours.

The resulting mixture is concentrated under vacuum. The residue obtained is taken up in aqueous sodium chloride solution and extracted twice with dichloromethane. The combined organic phases are dried over sodium sulfate, filtered and concentrated under reduced pressure. 8.50 g of an oily residue are obtained, which product is used without further purification in the following step.

7.1.2. methyl 2-(hydroxymethyl)oxazole-4-carboxylate 8.50 g (11.16 mmol) of ethyl 2-acetoxymethyloxazole-4-carboxylate, obtained in step 7.1.1., are dissolved in 280 mL of a 5/1 mixture of dichloromethane and methanol. 2.55 mL (11.16 mmol) of a 4.37N solution of sodium methoxide in methanol are added and the medium is stirred at room temperature for three hours.

The resulting mixture is cooled to 0° C., followed by addition of 10 mL of saturated aqueous ammonium chloride solution, and then concentrated under reduced pressure. The residue obtained is taken up in saturated aqueous sodium chloride solution and extracted three times with dichloromethane. The combined organic phases are washed once with saturated aqueous sodium chloride solution, dried over sodium sulfate, filtered and concentrated to dryness. The residue obtained is purified by chromatography on silica gel, eluting with a mixture from 99/1/0.1 to 97/3/0.3 of dichloromethane, methanol and 30% aqueous ammonia. 1.3 g of expected product are obtained in the form of a brown oil.

Melting point (° C.): 81-82° C.

$^1$H NMR (CDCl$_3$) δ (ppm): 8.25 (s, 1H); 4.85 (s, 2H); 4.00 (s, 3H); 3.50 (s, 1H).

7.2. [4-(methoxycarbonyl)oxazol-2-yl]methyl (3aR,5s,6aS)-5-(4-chlorophenoxy)hexahydrocyclopenta[c]pyrrole-2(1H)-carboxylate The process is performed according to the procedure described in Example 2, step 2.2. Starting with 0.15 g (0.63 mmol) of (3aR,5s,6aS)-5-(4-chlorophenoxy)octahydrocyclopenta[c]pyrrole, obtained in step 2.1., 0.12 g (0.82 mmol) of methyl 2-hydroxymethyloxazole-4-carboxylate, obtained in step 7.1.2., 0.15 g (0.76 mmol) of para-nitrophenyl chloroformate and 0.27 mL (1.58 mmol) of N,N-diisopropylethylamine, and after chromatography on silica gel, eluting with a 99/1/0.1 mixture of dichloromethane, methanol and aqueous ammonia, 0.24 g (90%) of expected product is obtained in the form of an oil.

7.3. [4-(methylcarbamoyl)oxazol-2-yl]methyl (3aR, 5s,6aS)-5-(4-chlorophenoxy)hexahydrocyclopenta[c]pyrrole-2(1H)-carboxylate The process is performed according to the procedure described in Example 5, step 5.4. Starting with 0.24 g (0.58 mmol) of [4-(methoxycarbonyl)oxazol-2-yl]methyl (3aR,5s,6aS)-5-(4-chlorophenoxy)hexahydrocyclopenta[c]-pyrrole-2(1H)-carboxylate, obtained in step 7.2., and 8.00 mL (64 mmol) of an 8N solution of methylamine in ethanol, and after chromatography on preparative silica gel plates, eluting with a 95/5/0.5 mixture of dichloromethane, methanol and aqueous ammonia, 0.11 g (45%) of expected product is obtained in the form of a white powder.

Melting point (° C.): 104-106° C.
LC-MS: M+H=420
$^1$H NMR (DMSO) δ (ppm): 8.60 (s, 1H); 8.25 (s, 1H); 7.30 (d, 2H); 6.95 (d, 2H); 5.20 (s, 2H); 4.95 (m, 1H); 3.55 (m, 2H); 3.20 (m, 2H); 2.85 (m, 2H); 2.80 (d, 3H); 2.05-1.95 (m, 2H); 1.95-1.80 (m, 2H).

EXAMPLE 8

Compound 31

(3-carbamoylisoxazol-5-yl)methyl (3aR,5s,6aS)-5-[(4'-fluorobiphenyl-4-yl)oxy]hexahydrocyclopenta[c]pyrrole-2(1H)-carboxylate (exo)

8.1. (3aR,5r,6aS)-octahydrocyclopenta[c]pyrrol-5-ol hydrochloride (1:1)

3.00 g (13.20 mmol) of tert-butyl (3aR,5r,6aS)-5-hydroxyhexahydrocyclopenta[c]pyrrole-2(1H)-carboxylate (see synthesis: WO 2006/108 059) are dissolved in 150 mL of a 2/1 mixture of dioxane and 1,2-dichloroethane. 30 mL (120 mmol) of a 4N solution of hydrogen chloride in dioxane are poured into the medium with stirring. After stirring for 3 hours at room temperature, the medium is concentrated to dryness and the product obtained in hydrochloride form is taken up in diethyl ether for organization of the salt. After filtering off and drying under reduced pressure, 1.745 g (81%) of the expected product are obtained in the form of a hygroscopic solid.

$^1$H NMR (DMSO) δ (ppm): 9.40 (s, 1H); 8.75 (s, 1H); 5.10 (s, 1H); 4.15 (tq, 1H); 3.25 (m, 2H); 3.10 (m, 2H); 2.80 (m, 2H); 1.85 (m, 2H); 1.55 (m, 2H).

8.2. [3-(ethoxycarbonyl)isoxazol-5-yl]methyl (3aR, 5r,6aS)-5-hydroxyhexahydrocyclopenta[c]pyrrole-2(1H)-carboxylate 0.627 g (3.67 mmol) of ethyl 5-(hydroxymethyl)isoxazole-3-carboxylate is dissolved in 10 mL of dichloromethane, 1.17 mL (6.72 mmol) of N,N-diisopropylethylamine are added and the medium is cooled to 0° C., followed by addition of a solution of 0.647 g (3.21 mmol) of 4-nitrophenyl chloroformate in 5 mL of dichloromethane. The medium is stirred for one hour at room temperature and then added slowly to a solution, cooled beforehand to −10° C., of 0.50 g (3.06 mmol) of (3aR,5r,6aS)-octahydrocyclopenta[c]pyrrol-5-ol hydrochloride, obtained in step 8.1., and 0.59 mL (3.36 mmol) of N,N-diisopropylethylamine in 15 mL of a 2/1 mixture of dichloromethane and methanol. After stirring for hours at room temperature, aqueous 1N sodium hydroxide solution is added and the medium is extracted three times with dichloromethane. The combined organic phases are washed once with saturated aqueous sodium chloride solution, dried over sodium sulfate, filtered and concentrated under reduced pressure. The residue obtained is purified by chromatography on silica gel, eluting with a 99/1 and then 98/2 mixture of dichloromethane and methanol. 0.78 g (79%) of the expected product is obtained in the form of an oil.

LC-MS: M+H=325
$^1$H NMR (DMSO) δ (ppm): 6.90 (s, 1H); 5.25 (s, 2H); 4.60 (d, 1H); 4.40 (dq, 2H); 4.10 (tq, 1H); 3.50 (m, 2H); 3.30 (m, 2H); 2.55 (m, 2H); 2.00 (m, 2H); 1.35 (m, 5H).

8.3. [3-(ethoxycarbonyl)isoxazol-5-yl]methyl (3aR, 5s,6aS)-5-(4-bromophenoxy)hexahydrocyclopenta[c]pyrrole-2(1H)-carboxylate 0.76 g (2.34 mmol) of [3-(ethoxycarbonyl)isoxazol-5-yl]methyl (3aR,5r,6aS)-5-hydroxyhexahydrocyclopenta[c]pyrrole-2(1H)-carboxylate, obtained in step 8.2., is dissolved in 24 mL of toluene. 0.737 g (2.81 mmol) of triphenylphosphine and 0.527 g (3.05 mmol) of 4-bromophenol are added, and the medium is then cooled to 0° C., followed by slow addition of a solution of 0.49 g (2.81 mmol) of diethyl azodicarboxylate in 3 mL of toluene. The medium is stirred for 14 hours at room temperature and then concentrated under vacuum. The residue obtained is taken up in aqueous 1N sodium hydroxide solution and extracted twice with dichloromethane. The combined organic phases are washed once with saturated aqueous sodium chloride solution, dried over sodium sulfate and concentrated under vacuum. The residue obtained is purified by chromatography on silica gel, eluting with dichloromethane and then with a 99/1 mixture of dichloromethane and methanol. 0.87 g (61%) of expected product is obtained in the form of a wax.

LC-MS: M+H=479
$^1$H NMR (DMSO) δ (ppm): 7.45 (d, 2H); 6.95 (s, 1H); 6.90 (d, 2H); 5.25 (s, 2H); 4.95 (tq, 1H); 4.35 (dq, 2H); 3.55 (m, 2H); 3.25 (m, 2H); 2.85 (m, 2H); 1.95 (m, 2H); 1.85 (m, 2H); 1.35 (t, 3H).

8.4. (3-carbamoylisoxazol-5-yl)methyl (3aR,5s,6aS)-5-(4-bromophenoxy)hexahydrocyclopenta[c]pyrrole-2(1H)-carboxylate The process is performed according to the procedure described in Example 5, step 5.4. Starting with 0.350 g (0.73 mmol) of [3-(ethoxycarbonyl)isoxazol-5-yl]methyl (3aR,5s,6aS)-5-(4-bromophenoxy)hexahydrocyclopenta[c]-pyrrole-2(1H)-carboxylate, obtained in step 8.3., in 5 mL of methanol and 5 mL (35 mmol) of a 7N solution of ammonia in methanol, and after chromatography on silica gel, eluting with a mixture from 99/1/0.1 to 98/2/0.2 of dichloromethane, methanol and aqueous ammonia, 0.072 g (59%) of the expected product is obtained in the form of a white powder.

Melting point (° C.): 132-134° C.
LC-MS: M+H=450
$^1$H NMR (DMSO) δ (ppm) 8.15 (s, 1H); 7.85 (s, 1H); 7.45 (d, 2H); 6.90 (d, 2H); 6.80 (s, 1H); 5.25 (s, 2H); 4.95 (tq, 1H); 3.55 (m, 2H); 3.20 (m, 2H); 2.85 (m, 2H); 2.22 (m, 2H); 1.85 (m, 2H).

8.5. (3-carbamoylisoxazol-5-yl)methyl (3aR,5s,6aS)-5-[(4'-fluorobiphenyl-4-yl)oxy]hexahydrocyclopenta[c]pyrrole-2(1H)-carboxylate Under an inert atmosphere, 0.20 g (0.44 mmol) of (3-carbamoylisoxazol-5-yl)methyl (3aR,5s,6aS)-5-(4-bromophenoxy)hexahydrocyclopenta[c]pyrrole-2(1H)-carboxylate, obtained in step 8.4., 0.074 g (0.53 mmol) of 4-fluoro-phenylboronic acid and 0.434 g (1.33 mmol) of caesium carbonate are placed in 11 mL of a 10/1 mixture of tetrahydrofuran and water. 0.036 g (0.04 mmol) of PdCl$_2$dppf.CH$_2$Cl$_2$ is added and the medium is then heated at about 75° C. for 15 hours.

After cooling to room temperature, the medium is taken up in dichloromethane and saturated aqueous sodium carbonate solution. The aqueous phase is extracted twice with dichloromethane and the combined organic phases are then washed with saturated aqueous sodium chloride solution, dried over sodium sulfate, filtered and concentrated under reduced pressure. The residue obtained is purified by chromatography on silica gel, eluting with dichloromethane and then with a 98/2/0.2 mixture of dichloromethane, methanol and 30% aqueous ammonia. 0.14 g (72%) of the expected product is obtained in the form of a white powder.
Melting point (° C.): 200-201° C.
LC-MS: MH–=464
$^1$H NMR (DMSO) δ (ppm): δ (ppm): 8.15 (s, 1H); 7.85 (s, 1H); 7.65 (t, 2H); 7.55 (d, 2H); 7.25 (t, 2H); 7.00 (d, 2H); 6.80 (s, 1H); 5.25 (s, 2H); 5.00 (m, 1H); 3.55 (m, 2H); 3.25 (m, 2H); 2.85 (m, 2H); 2.05 (m, 2H); 1.90 (m, 2H).

EXAMPLE 9

Compound 27

(3-carbamoylisoxazol-5-yl)methyl (3aR,5s,6aS)-5-[(4-chloro-1-naphthyl)oxy]hexahydrocyclopenta[c]pyrrole-2(1H)-carboxylate (exo)

9.1. [3-(ethoxycarbonyl)isoxazol-5-yl]methyl (3aR,5s,6aS)-5-[(4-chloro-1-naphthyl)oxy]hexahydrocyclopenta[c]pyrrole-2(1H)-carboxylate The process is performed according to the procedure described in Example 8, step 8.3. Starting with 0.60 g (1.85 mmol) of [3-(ethoxycarbonyl)isoxazol-5-yl]methyl (3aR,5r,6aS)-5-hydroxyhexahydrocyclopenta[c]pyrrole-2(1H)-carboxylate, obtained in step 8.2., 0.39 g (2.22 mmol) of 4-chloro-1-naphthol, 0.35 g (2.03 mmol) of diethyl azodicarboxylate and 0.58 g (2.22 mmol) of triphenylphosphine, and after chromatography on silica gel, eluting with dichloromethane and then with a 99/1 mixture of dichloromethane and methanol, 0.94 g (54%) of expected product is obtained in the form of an oil.
LC-MS: M+ (NH4+)=502
$^1$H NMR (DMSO) δ (ppm): 8.25 (d, 1H); 8.10 (d, 1H); 7.70 (t, 1H); 7.65 (t, 1H); 7.60 (d, 1H); 6.95 (d, 1H); 6.95 (s, 1H); 5.30 (s, 2H); 5.20 (tq, 1H); 4.40 (dq, 2H); 3.55 (m, 2H); 3.25 (m, 2H); 2.90 (m, 2H); 2.15 (m, 2H); 1.95 (m, 2H); 1.35 (t, 3H).

9.2. (3-carbamoylisoxazol-5-yl)methyl (3aR,5s,6aS)-5-[(4-chloro-1-naphthyl)oxy]hexahydrocyclopenta[c]pyrrole-2(1H)-carboxylate The process is performed according to the procedure described in Example 8, step 8.4. Starting with 0.40 g (0.82 mmol) of [3-(ethoxycarbonyl)isoxazol-5-yl]methyl (3aR,5s,6aS)-5-[(4-chloro-1-naphthyl)oxy]hexahydrocyclopenta[c]pyrrole-2(1H)-carboxylate, obtained in step 9.1., and 10 mL (70 mmol) of a 7M solution of ammonia in methanol, and after chromatography on silica gel, eluting with a mixture from 99/1/0.1 to 98/2/0.2 of dichloromethane, methanol and aqueous ammonia, 0.23 g (61%) of the expected product is obtained the form of a solid.
m.p. (° C.): 185-187
LC-MS: M+H=456
$^1$H NMR (DMSO) δ (ppm): 8.25 (d, 1H); 8.15 (d, 1H); 8.15 (s, 1H); 7.85 (s, 1H); 7.70 (t, 1H); 7.65 (t, 1H); 7.60 (d, 1H); 6.95 (d, 1H); 6.80 (s, 1H); 5.25 (s, 2H); 5.20 (m, 1H); 3.60 (m, 2H); 3.25 (m, 2H); 2.95 (m, 2H); 2.15 (m, 2H); 1.95 (m, 2H).

EXAMPLE 10

Compound 28

[3-(methylcarbamoyl)isoxazol-5-yl]methyl (3aR,5s,6aS)-5-[(4-chloro-1-naphthyl)oxy]hexahydrocyclopenta[c]pyrrole-2(1H)-carboxylate (exo)

The process is performed according to the procedure described in Example 8, step 8.4. Starting with 0.40 g (0.82 mmol) of [3-(ethoxycarbonyl)isoxazol-5-yl]methyl (3aR,5s,6aS)-5-[(4-chloro-1-naphthyl)oxy]hexahydrocyclopenta[c]pyrrole-2(1H)-carboxylate, obtained in step 9.1., and 10 mL (80 mmol) of an 8M solution of methylamine in ethanol, and after chromatography on silica gel, eluting with a 99/1/0.1 mixture of dichloromethane methanol and 30% aqueous ammonia, 0.16 g (55%) of the expected product is obtained in the form of a white powder.
m.p. (° C.): 131-133° C.
LC-MS: M+H=470
$^1$H NMR (DMSO) δ (ppm): 8.70 (s, 1H); 8.25 (d, 1H); 8.15 (d, 1H); 7.75 (t, 1H); 7.65 (t, 1H); 7.60 (d, 1H); 6.95 (d, 1H); 6.82 (s, 1H), 5.25 (s, 2H); 5.20 (m, 1H); 3.55 (m, 2H); 3.25 (m, 2H); 2.95 (m, 2H); 2.80 (d, 3H); 2.15 (m, 2H); 1.95 (m, 2H).

EXAMPLE 11

Compound 18 thiazol-2-ylmethyl (3aR,5s,6aS)-5-[(4'-ethoxybiphenyl-3-yl)oxy]hexahydrocyclopenta[c]pyrrole-2(1H)-carboxylate (exo)

11.1. tert-butyl (3aR,5s,6aS)-5-(3-bromophenoxy)hexahydrocyclopenta[c]pyrrole-2(1H)-carboxylate 0.20 g (0.88 mmol) of tert-butyl (3aR,5r,6aS)-5-hydroxyhexahydrocyclopenta[c]pyrrole-2(1H)-carboxylate (WO 2006/108 059), 0.19 g (1.10 mmol) of 3-bromophenol, 0.21 g (1.06 mmol) of diisopropyl azodicarboxylate and 0.34 g (1.09 mmol) of resin-supported triphenylphosphine (triphenylphosphine, polymer-supported, 3.2 mmol/g on polystyrene), are dissolved in 3.5 mL of toluene. The mixture is stirred at room temperature for 15 hours. After filtering off the resin, ethyl acetate is added and the organic phases are then washed with aqueous 1N sodium hydroxide solution. The organic phases are dried over sodium sulfate, filtered and concentrated under reduced pressure. The residue obtained is purified by chromatography on silica gel, eluting with a 95/5 and then 90/10 mixture of cyclohexane and ethyl acetate. 0.14 g (42%) of expected product is thus obtained in the form of an oil.

11.2. tert-butyl (3aR,5s,6aS)-5-[(4'-ethoxybiphenyl-3-yl)-oxy]hexahydrocyclopenta[c]pyrrole-2(1H)-carboxylate Under an inert atmosphere, 0.14 g (0.37 mmol) of tert-butyl (3aR,5s,6aS)-5-(3-bromophenoxy)hexahydrocyclopenta[c]-pyrrole-2(1H)-carboxylate, obtained in step 11.1., 0.08 g (0.51 mmol) of 4-ethoxyphenylboronic acid and 0.04 g (1.04 mmol) of lithium chloride are placed in 3.6 mL of a 1/1/0.4 mixture of ethanol, toluene and water. 0.46 mL (0.92 mmol) of aqueous 2M sodium carbonate solution and 0.02 g (0.02 mmol) of Pd(PPh$_3$)$_4$ are added to the medium. After heating for 15 hours at 75° C., the medium is allowed to cool to room temperature, and then taken up in ethyl acetate and water. The aqueous phase is extracted twice with ethyl acetate and then the combined organic phases are washed with saturated aqueous sodium chloride solution, dried over sodium sulfate, filtered and concentrated under reduced pressure. The residue obtained is purified by chromatography on silica gel, eluting with a 95/5 and then 90/10 mixture of cyclohexane and ethyl acetate. 0.088 g (57%) of expected product is thus obtained in the form of a wax.

11.3. (3aR,5s,6aS)-5-[(4'-ethoxybiphenyl-3-yl)oxy] octahydrocyclopenta[c]pyrrole The process is performed according to the procedure described in Example 1, step 1.2. Starting with 0.08 g (0.21 mmol) of tert-butyl (3aR,5s,6aS)-5-[(4'-ethoxybiphenyl-3-yl)oxy]hexahydrocyclopenta[c]pyrrole-2(1H)-carboxylate, obtained in step 11.2., and 1.04 mL of a 4N solution of hydrogen chloride in dioxane, 0.06 g (96%) of expected product is obtained in the form of an oil.

11.4. thiazol-2-ylmethyl (3aR,5s,6aS)-5-[(4'-ethoxybiphenyl-3-yl)oxy]hexahydrocyclopenta[c]pyrrole-2 (1H)-carboxylate The process is performed according to the procedure described in Example 1, step 1.3. Starting with 0.06 g (0.20 mmol) of (3aR,5s,6aS)-5-[(4'-ethoxybiphenyl-3-yl)oxy]-octahydrocyclopenta[c]pyrrole, obtained in step 11.3., 0.04 mL (0.22 mmol) of N,N-diisopropylethylamine and 0.05 g (0.18 mmol) of thiazol-4-ylmethyl 4-nitrophenyl carbonate (WO 2008/013 834), and after chromatography on silica gel, eluting with a 95/5 and then 90/10 mixture of cyclohexane and ethyl acetate, 0.05 g (69%) of expected product is obtained in the form of an oil.
LC-MS: M+H=465
$^1$H NMR (DMSO) δ (ppm): 7.80 (d, 1H); 7.75 (d, 1H); 7.60 (d, 2H); 7.35 (t, 1H); 7.15 (d, 1H); 7.05 (s, 1H); 7.00 (d, 2H); 6.85 (d, 1H); 5.35 (s, 2H); 5.10 (m, 1H); 4.10 (q, 2H); 3.55 (m, 2H); 3.30 (m, 2H); 2.90 (m, 2H); 2.10 (m, 2H); 1.90 (m, 2H); 1.40 (t, 3H)

EXAMPLE 12

Compound 1 thiazol-2-ylmethyl (3aR,5s,6aS)-5-(4-chlorophenoxy)hexahydrocyclopenta[c]pyrrole-2(1H)-carboxylate (exo)

12.1. thiazol-2-ylmethyl (3aR,5r,6aS)-5-hydroxyhexahydrocyclopenta[c]pyrrole-2(1H)-carboxylate The process is performed according to the procedure described in Example 1, step 1.3. Starting with 1.02 g (6.23 mmol) of (3aR,5r,6aS)-octahydrocyclopenta[c]pyrrol-5-ol hydrochloride, obtained according to step 8.1. of Example 8, 2.09 g (7.85 mmol) of thiazol-4-ylmethyl 4-nitrophenyl carbonate (WO 2008/013 834) and 3.25 mL (18.66 mmol) of N,N-diisopropylethylamine, and after chromatography on silica gel, eluting with a 98/2/0.2 and then 97/3/0.3 mixture of dichloromethane, methanol and 30% aqueous ammonia, 0.34 g (20%) of expected product is obtained in the form of a wax.

12.2. thiazol-2-ylmethyl (3aR,5s,6aS)-5-(4-chlorophenoxy)hexahydrocyclopenta[c]pyrrole-2(1H)-carboxylate The process is performed according to the procedure described in Example 11, step 11.1. Starting with 0.04 g (0.16 mmol) of 1,3-thiazol-2-ylmethyl (3aR,5r,6aS)-5-hydroxyhexahydrocyclopenta[c]pyrrole-2(1H)-carboxylate, obtained in step 12.1., 0.02 g (0.19 mmol) of 4-chlorophenol, 0.04 g (0.20 mmol) of diisopropyl azodicarboxylate and 0.08 g (0.25 mmol) of resin-supported triphenylphosphine (triphenylphosphine, polymer-supported, 3.2 mmol/g on polystyrene), and after chromatography on silica gel, eluting with a 95/5 and then 90/10 mixture of cyclohexane and ethyl acetate, 0.025 g (41%) of expected product is obtained the form of a solid.
m.p. (° C.): 75-77° C.
LC-MS: M+H=379
$^1$H NMR (DMSO) δ (ppm): 7.8 (d, 1H); 7.75 (d, 1H); 7.35 (d, 2H); 6.90 (d, 2H); 5.35 (s, 2H); 4.95 (m, 1H); 3.55 (m, 2H) 3.25 (broad m, 2H); 2.85 (broad m, 2H); 2.0 (m, 2H); 1.85 (m, 2H).

EXAMPLE 13

Compound 29 thiazol-4-ylmethyl (3aR,4S,6aS)-4-[(4-chloro-1-naphthyl)-oxy]hexahydrocyclopenta[c]pyrrole-2 (1H)-carboxylate (exo)

13.1. tert-butyl (3aR,4R,6aS)-4-hydroxyhexahydrocyclopenta[c]pyrrole-2(1H)-carboxylate Under an inert atmosphere, 1.00 g (4.44 mmol) of tert-butyl (3aR,6aS)-4-oxohexahydrocyclopenta[c]pyrrole-2 (1H)-carboxylate is dissolved in 15 mL of anhydrous tetrahydrofuran; the medium is cooled to −78° C. and 6.66 mL (6.66 mmol) of a solution of lithium tri-sec-borohydride (L-Selectride) at 1N in tetrahydrofuran are then added dropwise. The medium is allowed to warm to room temperature over three hours with stirring, and then cooled to 0° C., followed by dropwise addition of 35% aqueous hydrogen peroxide solution until the evolution of gas has ceased. The medium is diluted with water and extracted three times with ethyl acetate. The combined organic phases are washed once with saturated aqueous sodium chloride solution, dried over sodium sulfate, filtered and concentrated under reduced pressure. 0.826 g (82%) of the expected product is obtained in the form of a colourless oil.

13.2. tert-butyl (3aR,4S,6aS)-4-[(4-chloro-1-naphthyl)oxy]-hexahydrocyclopenta[c]pyrrole-2(1H)-carboxylate The process is performed according to the procedure described in Example 11, step 11.1. Starting with 0.15 g (0.66 mmol) of tert-butyl (3aR,4R,6aS)-4-hydroxyhexahydrocyclopenta[c]pyrrole-2(1H)-carboxylate, obtained in step 13.1., 0.130 g (0.73 mmol) of 4-chloro-1-naphthol, 0.160 g (0.79 mmol) of diisopropyl azodicarboxylate and 0.206 g (0.659 mmol) of resin-supported triphenylphosphine (triphenylphosphine, polymer-supported, 3.2 mmol/g on polysty-

13.3. (3aR,4S,6aS)-4-[(4-chloro-1-naphthyl)oxy] octahydrocyclopenta[c]pyrrole The process is performed according to the procedure described in Example 1, step 1.2. Starting with 0.103 g (0.27 mmol) of ter-butyl (3aR,4S,6aS)-4-[(4-chloro-1-naphthyl) oxy]hexahydrocyclopenta[c]pyrrole-2(1H)-carboxylate, obtained in step 13.2., and 1.33 mL of a 4N solution of hydrogen chloride in dioxane, and after chromatography on silica gel, eluting with a 97/3/0.3 and then 96/4/0.4 mixture of dichloromethane, methanol and 30% aqueous ammonia, 0.068 g (89%) of expected product is obtained in the form of a red oil.

13.4. thiazol-4-ylmethyl (3aR,4S,6aS)-4-[(4-chloro-1-naphthyl)oxy]hexahydrocyclopenta[c]pyrrole-2(1H)-carboxylate The process is performed according to the procedure described in Example 1, step 1.3. Starting with 0.059 g (0.21 mmol) of (3aR,4S,6aS)-4-[(4-chloro-1-naphthyl)oxy]-octahydrocyclopenta[c]pyrrole, obtained in step 13.3., 0.04 mL (0.25 mmol) of N,N-diisopropylethylamine and 0.066 g (0.23 mmol) of thiazol-4-ylmethyl 4-nitrophenyl carbonate (WO 2008/013 834), and after chromatography on silica gel, eluting with a 95/5 and then 90/10 mixture of cyclohexane and ethyl acetate, 0.017 g (19%) of expected product is obtained in the form of an oil.
LC-MS: M+H=429
$^1$H NMR (DMSO) δ (ppm): 9.10 (s, 1H); 8.25 (d, 1H); 8.15 (d, 1H); 7.75-7.60 (m, 4H); 7.00 (d, 1H); 5.20 (s, 2H); 4.90 (s, 1H); 3.70 (m, 1H); 3.60 (m, 1H); 3.30 (m, 2H); 2.90 (m, 2H); 2.20 (m, 2H); 1.90 (m, 1H); 1.55 (m, 1H).

EXAMPLE 14

Compound 30 thiazol-4-ylmethyl (3aR,4R,6aS)-4-[(4'-ethoxybiphenyl-3-yl)oxy]hexahydrocyclopenta[c]pyrrole-2(1H)-carboxylate (endo)

14.1. tert-butyl (3aR,4R,6aS)-4-(3-bromophenoxy)hexahydrocyclopenta[c]pyrrole-2(1H)-carboxylate The process is performed according to the procedure described in Example 1, step 1.1. Starting with 0.150 g (0.66 mmol) of tert-butyl (3aR,4R,6aS)-4-hydroxyhexahydrocyclopenta[c]pyrrole-2(1H)-carboxylate, obtained in step 13.1., 0.144 g (0.82 mmol) of 1-bromo-3-fluorobenzene, 0.024 g (0.99 mmol) of sodium hydride and 3 mL of N,N-dimethylformamide, and after chromatography on silica gel, 0.083 g (33%) of the expected product is obtained in the form of a colourless oil.

14.2. tert-butyl (3aR,4R,6aS)-4-[(4'-ethoxybiphenyl-3-yl)-oxy]hexahydrocyclopenta[c]pyrrole-2(1H)-carboxylate The process is performed according to the procedure described in Example 11, step 11.2. Starting with 0.123 g (0.324 mmol) of tert-butyl (3aR,4R,6aS)-4-(3-bromophenoxy)-hexahydrocyclopenta[c]pyrrole-2(1H)-carboxylate, obtained in step 14.1., 0.075 g (0.45 mmol) of 4-ethoxyphenylboronic acid, 0.039 g (0.91 mmol) of lithium chloride, 0.40 mL (0.80 mmol) of aqueous 2N sodium carbonate solution and 0.02 g (0.02 mmol) of Pd(PPh$_3$)$_4$, and after chromatography on silica gel, 0.105 g (77%) of the expected product is obtained in the form of a colourless oil.

14.3. (3aR,4R,6aS)-4-[(4'-ethoxybiphenyl-3-yl)oxy] octahydrocyclopenta[c]pyrrole The process is performed according to the procedure described in Example 1, step 1.2. Starting with 0.105 g (0.25 mmol) of tert-butyl (3aR,4R,6aS)-4-[(4'-ethoxybiphenyl-3-yl)oxy]hexahydrocyclopenta[c]pyrrole-2(1H)-carboxylate, obtained in step 14.2., and 1.24 mL of a 4N solution of hydrogen chloride in dioxane, and after chromatography on silica gel, 0.068 g (84%) of expected product is obtained in the form of an oil.

14.4. thiazol-4-ylmethyl (3aR,4R,6aS)-4-[(4'-ethoxybiphenyl-3-yl)oxy]hexahydrocyclopenta[c]pyrrole-2 (1H)-carboxylate The process is performed according to the procedure described in Example 1, step 1.3. Starting with 0.053 g (0.19 mmol) of (3aR,4R,6aS)-4-[(4'-ethoxybiphenyl-3-yl)oxy]octahydrocyclopenta[c]pyrrole, obtained in step 14.3., 0.04 mL (0.23 mmol) of N,N-diisopropylethylamine and 0.068 g (0.21 mmol) of thiazol-4-ylmethyl 4-nitrophenyl carbonate (WO 2008/013 834), and after chromatography on silica gel, eluting with a 95/5 and then a 90/10 mixture of cyclohexane and ethyl acetate, 0.055 g (63%) of expected product is obtained in the form of an oil.
LC-MS: M+H=465
$^1$H NMR (DMSO) δ (ppm): 9.10 (s, 1H); 7.70 (s, 1H); 7.60 (d, 2H); 7.35 (t, 1H); 7.20 (d, 1H); 7.10 (s, 1H); 7.00 (d, 2H); 6.90 (d, 1H); 5.20 (s, 2H); 4.90 (q, 1H); 4.10 (q, 2H); 3.60 (m, 2H); 3.30 (m, 2H); 3.05 (m, 1H); 2.80 (m, 1H); 2.10 (m, 1H); 1.85 (m, 2H); 1.55 (m, 1H); 1.35 (t, 3H).

EXAMPLE 15

Compound 40

(3-carbamoylisoxazol-5-yl)methyl (3aR,5r,6aS)-5-(4-fluoro-1,3-benzothiazol-2-yl)-5-hydroxyhexahydrocyclopenta[c]-pyrrole-2(1H)-carboxylate (exo)

15.1 4-fluoro-2-benzothiazole 2.00 g (10.14 mmol) of 4-fluoro-2-benzothiazolecarboxylic acid are dissolved in 50 mL of an equal-volume mixture of toluene and ethanol. 2.508 g (13.19 mmol) of para-toluenesulfonic acid monohydrate are added. After refluxing for 14 hours, the medium is concentrated to dryness and the residue is taken up in saturated aqueous sodium carbonate solution. The aqueous phase is extracted twice and the combined organic phases are then washed once with saturated aqueous sodium chloride solution, dried over sodium sulfate and concentrated under reduced pressure. 1.5 g (97%) of expected product are obtained in the form of an oil.

15.2 tert-butyl (3aR,5r,6aS)-5-(4-fluoro-1,3-benzothiazol-2-yl)-5-hydroxyhexahydrocyclopenta[c]pyrrole-2(1H)-carboxylate Under an inert atmosphere, 1 g (6.53 mmol) of 4-fluoro-2-benzothiazole (obtained in step 15.1) is dissolved in 30 mL of tetrahydrofuran. The medium is cooled to −78° C. and 4.49 mL (7.18 mmol) of a 1.6 M solution of n-butyllithium are added dropwise. The medium is allowed to warm to 0° C. and then cooled again to −78° C., followed by addition of a solution of 1.618 g (7.18 mmol) of tert-butyl (3aR,6aS)-5-oxohexahydrocyclopenta[c]pyrrole-2(1H)-carboxylate in 5 mL of tetrahydrofuran. The medium is allowed to cool to room temperature with stirring for one hour and then hydrolysed with saturated aqueous ammonium chloride solution. The medium is extracted three times with dichloromethane and the combined organic phases are then washed once with saturated aqueous sodium chloride solution, dried over sodium sulfate and then concentrated under vacuum. After chromatography on silica gel, eluting with dichloromethane and then with a 99/1/0.1 mixture of dichloromethane, methanol and 30% aqueous ammonia, and reorganization of the solid obtained in diethyl ether, 1 g (41%) of the expected product is obtained in the form of a white powder.

LC-MS: M+H=379

$^1$H NMR (DMSO) δ (ppm): 7.95 (d, 1H); 7.45 (m, 1H); 7.35 (t, 1H); 6.45 (s, 1H); 3.55 (t, 2H); 3.35 (m, 2H); 3.00 (m, 2H); 2.45 (m, 2H); 2.00 (d, 2H); 1.45 (s, 9H).

15.3 (3aR,5r,6aS)-5-(4-fluoro-1,3-benzothiazol-2-yl)octahydrocyclopenta[c]pyrrol-5-ole hydrochloride 0.50 g (1.32 mmol) of tert-butyl (3aR,5r,6aS)-5-(4-fluoro-1,3-benzothiazol-2-yl)-5-hydroxyhexahydrocyclopenta[c]-pyrrole-2(1H)-carboxylate is dissolved in 30 mL of dichloromethane. 5.00 mL (20.00 mmol) of a 4N solution of hydrogen chloride in dioxane are added slowly to the medium cooled to −5° C. with stirring, and the medium is then allowed to cool to room temperature with stirring for 14 hours. The medium is concentrated to dryness under reduced pressure. After reorganization of the residue obtained in diethyl ether and filtration, 0.388 g (93%) of the expected product is obtained in the form of a brown powder.

LC-MS: M+H=279

$^1$H NMR (DMSO) δ (ppm): 7.95 (d 1H); 7.45 (m, 1H); 7.35 (t, 1H); 3.45 (t, 2H); 3.25 (m, 2H); 3.15 (m, 2H); 2.45 (m, 2H); 2.15 (d, 2H).

15.4 (3-carbamoylisoxazol-5-yl)methyl (3aR,5r,6aS)-5-(4-fluoro-1,3-benzothiazol-2-yl)-5-hydroxyhexahydrocyclopenta[c]pyrrole-2(1H)-carboxylate In a sealed tube, 0.380 g (1.21 mmol) of (3aR,5r,6aS)-5-(4-fluoro-1,3-benzothiazol-2-yl)octahydrocyclopenta[c]pyrrol-5-ole hydrochloride is suspended in 6 mL of 1,2-dichloroethane. 0.408 g (1.33 mmol) of 3-carbamoylisoxazol-5-ylmethyl 4-nitrophenyl carbonate, obtained in step 4.2., 0.074 g (0.60 mmol) of N,N-dimethylaminopyridine and 0.63 mL (3.62 mmol) of N,N-diisopropylethylamine are added and the medium is stirred for 10 minutes at room temperature, followed by heating at 70° C. for 4 hours with stirring. The medium is allowed to cool to room temperature, and is diluted with dichloromethane and aqueous 1N sodium hydroxide solution. The aqueous phase is extracted twice with dichloromethane and the combined organic phases are then washed once with saturated aqueous ammonium chloride solution and once with saturated aqueous sodium chloride solution, dried over sodium sulfate, filtered and concentrated under vacuum. After chromatography on the residue on silica gel, eluting with a 99/1/0.1 and then a 98/2/0.2 mixture of dichloromethane, methanol and 30% aqueous ammonia, 0.392 g (72%) of the expected product is obtained in the form of a white powder.

m.p. (° C.): 173-174° C.

LC-MS: M+H=447

$^1$H NMR (DMSO) δ (ppm): 8.15 (s, 1H); 7.90 (d, 1H); 7.85 (s, 1H); 7.40 (t, 1H); 7.35 (t, 1H); 6.80 (s, 1H); 6.45 (s, 1H); 5.25 (s, 2H); 3.65 (m, 2H); 3.45 (d, 2H); 3.00 (m, 2H); 2.50 (m, 2H); 2.00 (d, 2H).

EXAMPLE 16

Compound 42

(3-{[2-(dimethylamino)ethyl]carbamoyl}isoxazol-5-yl)methyl (3aR,5s,6aS)-5-(4-fluorophenoxy)hexahydrocyclopenta[c]pyrrole-2(1H)-carboxylate (exo)

16.1. [3-(ethoxycarbonyl)isoxazol-5-yl]methyl (3aR,5s,6aS)-5-(4-fluorophenoxy)hexahydrocyclopenta[c]pyrrole-2(1H)-carboxylate The process is performed according to the procedure described in Example 8, step 8.3. Starting with 0.70 g (2.16 mmol) of [3-(ethoxycarbonyl)isoxazol-5-yl]methyl (3aR,5r,6aS)-5-hydroxyhexahydrocyclopenta[c]pyrrole-2(1H)-carboxylate obtained in step 8.2., 0.679 g (2.59 mmol) of triphenylphosphine, 0.290 g (2.59 mmol) of 4-fluorophenol and 0.451 g (2.59 mmol) of diethyl azodicarboxylate, and after chromatography on silica gel, eluting with dichloromethane and then with a 99/1 mixture of dichloromethane and methanol, 0.80 g (88.6%) of expected product is obtained in the form of a brown wax.

LC-MS: M+H=419

$^1$H NMR (CDCl$_3$) δ (ppm): 6.90 (t, 2H); 6.70 (m, 3H); 5.15 (s, 2H); 4.75 (tq, 1H); 4.35 (dq, 2H); 3.55 (m, 2H); 3.25 (m, 2H); 2.85 (m, 2H); 2.10 (m, 2H); 1.70 (m, 2H); 1.35 (t, 3H).

16.2. (3-{[2-(dimethylamino)ethyl]carbamoyl}isoxazol-5-yl)-methyl (3aR,5s,6aS)-5-(4-fluorophenoxy)hexahydrocyclopenta[c]pyrrole-2(1H)-carboxylate (hydrochloride 1/1))

0.40 g (0.96 mmol) of [3-(ethoxycarbonyl)isoxazol-5-yl]-methyl (3aR,5s,6aS)-5-(4-fluorophenoxy)hexahydrocyclopenta[c]pyrrole-2(1H)-carboxylate and 0.084 g (0.96 mmol) of N,N-dimethylethylenediamine are dissolved in 5 mL of methanol. The medium is heated for 4 hours at 60° C. and then allowed to cool to room temperature and concentrated to dryness. The residue is purified by chromatography on silica gel, eluting with a 97/3/0.3 and then 95/5/0.5 mixture of dichloromethane, methanol and 30% aqueous ammonia. 0.267 g (60.7%) of the expected product is obtained in the form of an oil, which is dissolved in 10 mL of dichloromethane. 1 mL of a 4N solution of hydrogen chloride in dioxane is added and the medium is stirred for one hour and then concentrated under reduced pressure. After reorganization of the residue in diethyl ether, filtering and drying under vacuum, 0.262 g (90.9%) of the corresponding expected hydrochloride is obtained in the form of a white powder.

Melting point (° C.): 146-148° C.

LC-MS: M+H=461

$^1$H NMR (DMSO) δ (ppm): 10.10 (broad s, 1H); 9.05 (t, 1H); 7.10 (t, 2H); 6.95 (m, 3H); 5.25 (s, 2H); 4.90 (m, 1H); 3.65 (m, 2H); 3.55 (m, 2H); 3.25 (m, 2H); 3.20 (m, 2H); 2.85 (s, 8H); 2.00 (m, 2H); 1.85 (m, 2H).

EXAMPLE 17

Compound 34

(3-carbamoylisoxazol-5-yl)methyl (3aR,5s,6aS)-5-(4-chloro-3-fluorophenoxy)hexahydrocyclopenta[c]pyrrole-2(1H)-carboxylate (exo)

17.1. (3aR,5s,6aS)-5-(4-chloro-3-fluorophenoxy)octahydrocyclopenta[c]pyrrole The process is performed according to the procedure described in Example 2, step 2.1. Starting with 5.0 g (22.00 mmol) of tert-butyl (3aR,5r,6aS)-5-hydroxyhexahydrocyclopenta[c]pyrrole-2(1H)-carboxylate (see synthesis: WO 2006/108 059), 3.87 g (26.40 mmol) of 4-chloro-3-fluorophenol, 4.41 g (25.30 mmol) of diethyl azodicarboxylate, 6.64 g (25.30 mmol) of triphenylphosphine and 20 mL of a 4N solution of hydrogen chloride in dioxane, 4.86 g (86.5%) of expected product are obtained in the form of a wax.

LC-MS: M+H=256

$^1$H NMR (CDCl$_3$) δ (ppm): 7.25 (t, 1H); 6.65 (m, 2H); 4.85 (tq, 1H); 3.05-2.70 (m, 6H); 2.20 (m, 2H); 1.60 (m, 2H).

17.2. (3-carbamoylisoxazol-5-yl)methyl (3aR,5s,6aS)-5-(4-chloro-3-fluorophenoxy)hexahydrocyclopenta[c]pyrrole-2(1H)-carboxylate The process is performed according to the procedure described in Example 1, step 1.3. Starting with 1.20 g (4.69 mmol) of (3aR,5s,6aS)-5-(4-chloro-3-fluorophenoxy)-octahydrocyclopenta[c]pyrrole, obtained in step 17.1., 1.73 g (5.63 mmol) of 3-carbamoylisoxazol-5-ylmethyl 4-nitrophenyl carbonate, obtained in step 4.2., 0.287 g (2.35 mmol) of N,N-dimethylaminopyridine and 2.04 mL (11.73 mmol) of N,N-diisopropylethylamine, and after chromatography on silica gel, eluting with a 98/2/0.2 mixture of dichloromethane, methanol and 30% aqueous ammonia, 1.45 g (73%) of expected product are obtained in the form of a white powder.

Melting point (° C.): 100-102° C.

LC-MS: M+H=424

$^1$H NMR (DMSO) δ (ppm): 8.15 (s, 1H); 7.85 (s, 1H); 7.45 (t, 1H); 7.05 (m, 1H); 6.80 (d, 2H); 5.25 (s, 2H); 5.00 (m, 1H); 3.55 (m, 2H); 3.20 (d, 2H); 2.85 (m, 2H); 2.00 (m, 2H); 1.90 (m, 2H).

Table 1 below illustrates the chemical structures and physical properties of a few compounds according to the invention.

In this table:

all the compounds are in free base form with the exception of the compound of Example 42, which is in the form of the hydrochloride in a base/salt proportion of 1/1;

TABLE 1

TABLE 1-continued

| No. | R₁ | m | n | o | p | A | R₂ | R₃ | endo/exo | R₄ |
|---|---|---|---|---|---|---|---|---|---|---|
| 6. | 4'-ethoxybiphenyl-3-yl | 1 | 1 | 1 | 1 | O | H | H | endo | thiazol-2-yl |
| 7. | 4-Cl-phenyl | 1 | 1 | 1 | 1 | O | H | H | exo | 1,2,3-thiadiazol-4-yl |
| 8. | 4-Cl-phenyl | 1 | 1 | 1 | 1 | O | H | H | exo | 5-tert-butyl-1,3,4-thiadiazol-2-yl |
| 9. | 4-F-phenyl | 1 | 1 | 1 | 1 | O | H | H | exo | 1,2,3-thiadiazol-4-yl |
| 10. | 4-F-phenyl | 1 | 1 | 1 | 1 | O | H | H | exo | 5-carbamoyl-isoxazol-3-yl |
| 11. | 4-Cl-phenyl | 1 | 1 | 1 | 1 | O | H | H | exo | 5-(N-methylcarbamoyl)-isoxazol-3-yl |
| 12. | 4-Cl-phenyl | 1 | 1 | 1 | 1 | O | H | H | exo | 5-carbamoyl-isoxazol-3-yl |
| 13. | 4-Cl-phenyl | 1 | 1 | 1 | 1 | O | H | H | exo | 1-methyl-1,2,4-triazol-5-yl |
| 14. | 4-Cl-phenyl | 1 | 1 | 1 | 1 | O | H | H | exo | 4-carbamoyl-thiazol-2-yl |
| 15. | 4-Cl-phenyl | 1 | 1 | 1 | 1 | O | H | H | exo | 4-(N-methylcarbamoyl)-thiazol-2-yl |

TABLE 1-continued

| No. | R₁ | m | n | o | p | A | R₂ | R₃ | endo/exo | R₄ |
|---|---|---|---|---|---|---|---|---|---|---|
| 16. | 3-(trifluoromethyl)phenyl | 1 | 1 | 1 | 1 | O | H | H | exo | isoxazole-3-carboxamide (5-yl) |
| 17. | 3-(trifluoromethyl)phenyl | 1 | 1 | 1 | 1 | O | H | H | exo | 5-(N-methyl)isoxazole-3-carboxamide |
| 18. | 4'-ethoxy-[1,1'-biphenyl]-3-yl | 1 | 1 | 1 | 1 | O | H | H | exo | thiazol-2-yl |
| 19. | 4-chlorophenyl | 1 | 1 | 1 | 1 | O | H | H | exo | oxazole-4-carboxamide (2-yl) |
| 20. | 6-methoxynaphthalen-2-yl | 1 | 0 | 1 | 2 | O | H | H | exo | thiazol-4-yl |
| 21. | 3-(trifluoromethyl)phenyl | 1 | 0 | 1 | 2 | O | H | H | endo | thiazol-4-yl |
| 22. | 7-ethoxynaphthalen-2-yl | 1 | 1 | 1 | 1 | O | H | H | exo | thiazole-4-carboxamide (2-yl) |
| 23. | 7-ethoxynaphthalen-2-yl | 1 | 1 | 1 | 1 | O | H | H | exo | 2-(N-methyl)thiazole-4-carboxamide |
| 24. | 7-ethoxynaphthalen-2-yl | 1 | 1 | 1 | 1 | O | H | H | exo | isoxazole-3-carboxamide (5-yl) |

TABLE 1-continued
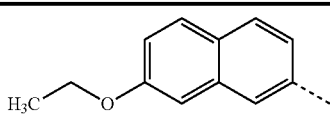
| No. | R₁ | m | n | o | p | A | R₂ | R₃ | endo/exo | R₄ |
|-----|----|---|---|---|---|---|----|----|----------|----|
| 25. | 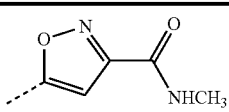 | 1 | 1 | 1 | 1 | O | H | H | exo | 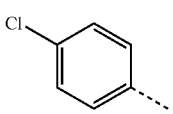 |
| 26. | 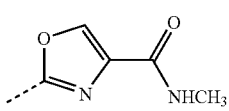 | 1 | 1 | 1 | 1 | O | H | H | exo | 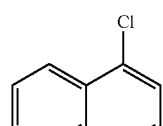 |
| 27. | 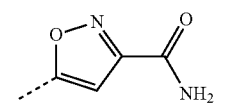 | 1 | 1 | 1 | 1 | O | H | H | exo | 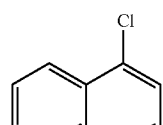 |
| 28. | 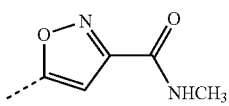 | 1 | 1 | 1 | 1 | O | H | H | exo | 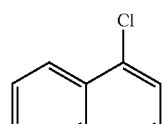 |
| 29. | 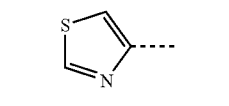 | 1 | 0 | 1 | 2 | O | H | H | exo | 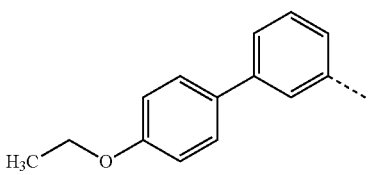 |
| 30. | 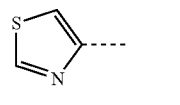 | 1 | 0 | 1 | 2 | O | H | H | endo | 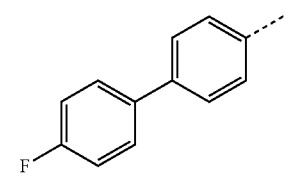 |
| 31. | 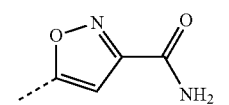 | 1 | 1 | 1 | 1 | O | H | H | exo | 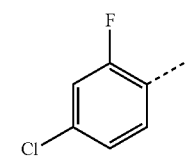 |
| 32. | 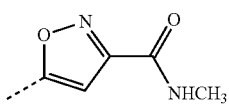 | 1 | 1 | 1 | 1 | O | H | H | exo | |

TABLE 1-continued

| No. | R₁ | m | n | o | p | A | R₂ | R₃ | endo/exo | R₄ |
|---|---|---|---|---|---|---|---|---|---|---|
| 33. | 4-chloro-2-fluorophenyl | 1 | 1 | 1 | 1 | O | H | H | exo | 5-carbamoyl-isoxazol-3-yl |
| 34. | 3-fluoro-4-chlorophenyl | 1 | 1 | 1 | 1 | O | H | H | exo | 5-carbamoyl-isoxazol-3-yl |
| 35. | 3-fluoro-4-chlorophenyl | 1 | 1 | 1 | 1 | O | H | H | exo | 5-(N-methylcarbamoyl)-isoxazol-3-yl |
| 36. | 2,4-dichlorophenyl | 1 | 1 | 1 | 1 | O | H | H | exo | 5-carbamoyl-isoxazol-3-yl |
| 37. | 2,4-dichlorophenyl | 1 | 1 | 1 | 1 | O | H | H | exo | 5-(N-methylcarbamoyl)-isoxazol-3-yl |
| 38. | isoquinolin-7-yl | 1 | 1 | 1 | 1 | O | H | H | exo | 5-carbamoyl-isoxazol-3-yl |
| 39. | isoquinolin-6-yl | 1 | 1 | 1 | 1 | O | H | H | exo | 5-carbamoyl-isoxazol-3-yl |
| 40. | 4-fluorobenzothiazol-2-yl | 1 | 1 | 1 | 1 | bond | OH | H | exo | 5-carbamoyl-isoxazol-3-yl |
| 41. | 7-ethoxynaphthalen-2-yl | 1 | 1 | 1 | 1 | O | H | H | exo | 2-carbamoyl-oxazol-4-yl |

TABLE 1-continued

| No. | R₁ | m | n | o | p | A | R₂ | R₃ | endo/exo | R₄ |
|---|---|---|---|---|---|---|---|---|---|---|
| 42. | 4-fluorophenyl | 1 | 1 | 1 | 1 | O | H | H | exo | isoxazole-C(O)NH-CH₂CH₂-N(CH₃)₂ |
| 43. | 7-ethoxynaphthalen-2-yl | 1 | 1 | 1 | 1 | O | H | H | exo | oxazole-C(O)NH-CH₃ |
| 44. | 4-fluorophenyl | 1 | 1 | 1 | 1 | O | H | H | exo | isoxazole-C(O)N(CH₃)₂ |
| 45. | 4'-fluorobiphenyl-4-yl | 1 | 1 | 1 | 1 | O | H | H | exo | isoxazole-C(O)NH-CH₃ |

Table 2 below gives the results of the $^1$H NMR analyses, the melting points (m.p.) and the masses M+H measured (or M−H when the value is marked with an asterisk as for compound 31, whose M−H=464*) for the compounds of Table 1.

TABLE 2

| No. | $^1$H NMR 400 MHz DMSO | m.p. | M + H |
|---|---|---|---|
| 1 | 7.8 (d, 1H); 7.75 (d, 1H); 7.35 (d, 2H); 6.90 (d, 2H); 5.35 (s, 2H); 4.95 (m, 2H); 3.55 (m, 2H); 3.25 (broad m, 2H); 2.85 (broad m, 2H); 2.0 (m, 2H); 1.85 (m, 2H). | 75-77° C. | 379 |
| 2 | 7.85 (d, 1H); 7.75 (d, 1H); 7.60 (d, 2H); 7.10 (d, 2H); 5.35 (s, 2H); 5.00 (broad s, 1H); 3.55 (broad m, 2H); 3.30 (broad m, 2H); 2.85 (broad m, 2H); 2.05 (m, 2H); 1.90 (m, 2H). | 65-67° C. | 413 |
| 3 | 7.80 (d, 1H); 7.70 (d, 1H); 7.65 (d, 2H); 7.15 (t, 2H); 6.95 (t, 2H); 5.35 (s, 2H); 5.05 (broad s, 1H); 4.10 (q, 2H); 3.65 (broad m, 2H); 3.25 (broad m, 2H); 2.85 (broad m, 2H); 2.10 (m, 2H); 1.95 (m, 2H); 1.40 (t, 3H). | 69-71° C. | 339 |
| 4 | 7.80 (d, 1H); 7.75 (d, 1H); 7.50 (t, 1H); 7.30 (d, 1H); 7.20 (d, 1H); 7.15 (d, 1H); 5.25 (s, 2H); 4.95 (m, 1H); 3.55 (m, 2H); 3.40 (m, 2H); 2.80 (m, 2H); 2.30 (m, 2H); 1.70 (m, 2H) | oil | 413 |
| 5 | 7.80 (d, 1H); 7.75 (d, 1H); 7.50 (t, 1H); 7.30 (d, 1H); 7.20 (s, 1H); 7.15 (d, 1H); 5.35 (s, 2H); 5.05 (m, 1H); 3.50 (m, 2H); 3.25 (m, 2H); 2.85 (m, 2H); 2.00 (m, 2H); 1.90 (m, 2H). | oil | 413 |
| 6 | 7.80 (d, 1H); 7.70 (d, 1H); 7.60 (d, 2H); 7.30 (t, 1H); 7.15 (d, 1H); 7.05 (s, 1H); 7.00 (d, 2H); 6.80 (d, 1H); 5.35 (d, 2H); 5.00 (m, 1H); 4.10 (q, 2H); 3.55 (m, 2H); 3.35 (m, 2H); 2.75 (m, 2H); 2.30 (m, 2H); 1.70 (m, 2H); 1.35 (t, 3H) | oil | 465 |
| 7 | δ (ppm): 9.20 (s, 1H); 7.30 (d, 2H); 6.90 (d, 2H); 5.55 (s, 2H); 4.95 (m, 1H); 3.55 (m, 2H); 3.20 (m, 2H); 2.80 (m, 2H); 2.05-1.90 (m, 2H); 1.90-1.80 (m, 2H). | 122-124° C. | 380 |
| 8 | δ (ppm): 7.30 (d, 2H); 6.90 (d, 2H); 5.4 (s, 2H); 4.95 (m, 1H); 3.55 (m, 2H); 3.25 (m, 2H); 2.85 | wax | 436 |

TABLE 2-continued

| No. | ¹H NMR 400 MHz DMSO | m.p. | M + H |
|---|---|---|---|
|  | (m, 2H); 2.00 (m, 2H); 1.90 (m, 2H); 1.45 (s, 9H). |  |  |
| 9 | δ (ppm): 9.20 (s, 1H); 7.10 (m, 2H); 6.90 (m, 2H); 5.55 (s, 2H); 4.90 (m, 1H); 3.55 (m, 2H); 3.20 (m, 2H); 2.80 (m, 2H); 2.05-1.90 (m, 2H); 1.90-1.80 (m, 2H). | 93-95° C. | 364 |
| 10 | δ (ppm): 8.15 (s, 1H); 7.85 (s, 1H); 7.10 (m, 2H); 6.90 (m, 2H); 6.80 (s, 1H); 5.25 (s, 2H); 4.95 (m, 1H); 3.55 (m, 2H); 3.20 (m, 2H); 2.80 (m, 2H); 2.05-1.90 (m, 2H); 1.90-1.80 (m, 2H). | 151-152° C. | 390 |
| 11 | δ (ppm): 8.70 (s, 1H); 7.30 (d, 2H); 6.95 (d, 2H); 6.80 (s, 1H); 5.25 (s, 2H); 4.95 (m, 1H); 3.55 (m, 2H); 3.25 (m, 2H); 2.85 (m, 2H); 2.80 (d, 3H); 2.05-1.90 (m, 2H); 1.90-1.80 (m, 2H). | 117-118° C. | 420 |
| 12 | δ (ppm): 8.15 (s, 1H); 7.85 (s, 1H); 7.30 (d, 2H); 6.90 (d, 2H); 6.80 (s, 1H); 5.25 (s, 2H); 4.95 (m, 1H); 3.55 (m, 2H); 3.20 (m, 2H); 2.85 (m, 2H); 2.05-1.90 (m, 2H); 1.90-1.80 (m, 2H). | 126-127° C. | 406 |
| 13 | δ (ppm): 7.90 (s, 1H); 7.30 (d, 2H); 6.90 (d, 2H); 5.25 (s, 2H); 4.95 (m, 1H); 3.90 (m, 3H); 3.55 (m, 2H); 3.20 (m, 2H); 2.80 (m, 2H); 2.05-1.90 (m, 2H); 1.90-1.80 (m, 2H). | 58-60° C. | 377 |
| 14 | δ (ppm): 8.25 (s, 1H); 7.75 (s, 1H); 7.55 (s, 1H); 7.30 (d, 2H); 6.90 (d, 2H); 5.35 (s, 2H); 4.95 (m, 1H); 3.55 (m, 2H); 3.25 (m, 2H); 2.85 (m, 2H); 2.05-1.90 (m, 2H); 1.90-1.80 (m, 2H). | 171-173° C. | 422 |
| 15 | δ (ppm): 8.35 (m, 1H); 8.25 (s, 1H); 7.30 (d, 2H); 6.95 (d, 2H); 5.35 (s, 2H); 4.95 (m, 1H); 3.55 (m, 2H); 3.25 (m, 2H); 2.85 (m, 2H); 2.80 (d, 3H); 2.05-1.95 (m, 2H); 1.95-1.80 (m, 2H). | 129-131° C. | 436 |
| 16 | δ (ppm): 8.15 (s, 1H); 7.85 (s, 1H); 7.55 (t, 1H); 7.25 (d, 1H); 7.20 (d, 1H); 7.15 (s, 1H); 6.80 (s, 1H); 5.25 (s, 2H); 5.10 (m, 1H); 3.55 (m, 2H); 3.20 (m, 2H); 2.85 (m, 2H); 2.05-1.95 (m, 2H); 1.95-1.80 (m, 2H). | 130-132° C. | 440 |
| 17 | δ (ppm): 8.70 (s, 1H); 7.50 (t, 1H); 7.25 (d, 1H); 7.20 (d, 1H); 7.15 (s, 1H); 6.80 (s, 1H); 5.25 (s, 2H); 5.10 (m, 1H); 3.55 (m, 2H); 3.25 (m, 2H); 2.85 (m, 2H); 2.80 (s, 2H); 2.10-2.00 (m, 2H); 2.00-1.85 (m, 2H). | 98-100° C. | 454 |
| 18 | 7.80 (d, 1H); 7.75 (d, 1H); 7.60 (d, 2H); 7.35 (t, 1H); 7.15 (d, 1H); 7.05 (s, 1H); 7.00 (d, 2H); 6.85 (d, 1H); 5.35 (s, 2H); 5.10 (m, 1H); 4.10 (q, 2H); 3.55 (m, 2H); 3.30 (m, 2H); 2.90 (m, 2H); 2.10 (m, 2H); 1.90 (m, 2H); 1.40 (t, 3H) | oil | 465 |
| 19 | δ (ppm): 8.60 (s, 1H); 7.65 (s, 1H); 7.50 (s, 1H); 7.30 (d, 2H); 6.90 (d, 2H); 5.20 (s, 2H); 4.95 (m, 1H); 3.55 (m, 2H); 3.20 (m, 2H); 2.80 (m, 2H); 2.05-1.95 (m, 2H); 1.95-1.80 (m, 2H). | 139-141° C. | 406 |
| 20 | 9.10 (s, 1H); 7.75 (m, 3H); 7.20 (broad s, 2H); 7.10 (m, 2H); 5.20 (s, 2H); 4.80 (s, 1H); 3.85 (s, 3H); 3.70 (m, 1H); 3.55 (m, 1H); 3.35 (m, 1H); 3.25 (m, 1H); 2.80 (m, 2H); 2.15 (m, 1H); 2.05 (m, 1H); 1.80 (m, 1H); 1.55 (m, 1H) | oil | 425 |
| 21 | 9.15 (s, 1H); 7.65 (m, 1H); 7.55 (m, 1H); 7.25 (m, 3H); 5.20 (s, 2H); 4.95 (m, 1H); 3.60 (m, 2H); 3.30 (m, 2H); 3.05 (m, 1H); 2.80 (m, 1H); 2.05 (m, 1H); 1.90 (m, 2H); 1.55 (m, 1H) | oil | 413 |
| 22 | δ (ppm): 8.30 (s, 1H); 7.75 (d, 2H); 7.75 (s, 1H); 7.60 (s, 1H); 7.20 (m, 2H); 6.95 (m, 2H); 5.40 (s, 2H); 5.10 (m, 1H); 4.15 (dq, 2H); 3.60 (m, 2H); 3.25 (m, 2H); 2.90 (m, 2H); 2.15-2.05 (m, 2H); 2.05-1.90 (m, 2H); 1.40 (t, 3H). | 143-145° C. | 482 |
| 23 | δ (ppm): 8.40 (m, 1H); 8.25 (s, 1H); 7.75 (d, 2H); 7.20 (m, 2H); 6.95 (m, 2H); 5.40 (s, 2H); 5.10 (m, 1H); 4.15 (dq, 2H); 3.60 (m, 2H); 3.25 (m, 2H); 2.90 (m, 2H); 2.80 (d, 3H); 2.15-2.05 (m, 2H); 2.05-1.90 (m, 2H); 1.40 (t, 3H). | 149-151° C. | 496 |
| 24 | δ (ppm): 8.11 (s, 1H); 7.82 (s, 1H); 7.69 (d, 2H); 7.18 (s, 1H); 7.17 (s, 1H); 6.95 (m, 2H); 6.80 (s, 1H); 5.24 (s, 2H); 5.06 (m, 1H); 4.12 (dq, 2H); 3.56 (m, 2H); 3.23 (m, 2H); 2.85 (m, 2H); 2.07 (m, 2H); 1.94 (m, 2H); 1.38 (t, 3H). | 162-164° C. | 466 |
| 25 | δ (ppm): 8.69 (s, 1H); 7.69 (d, 2H); 7.18 (s, 1H); 7.16 (s, 1H); 6.95 (m, 2H); 6.81 (s, 1H); 5.25 (s, 2H); 5.06 (m, 1H); 4.12 (dq, 2H); 3.56 (m, 2H); 3.23 (m, 2H); 2.85 (m, 2H); 2.77 (d, 3H); 2.06 (m, 2H); 1.94 (m, 2H); 1.38 (t, 3H). | 108-110° C. | 480 |
| 26 | δ (ppm): 8.60 (s, 1H); 8.25 (s, 1H); 7.30 (d, 2H); 6.95 (d, 2H); 5.20 (s, 2H); 4.95 (m, 1H); 3.55 (m, 2H); 3.20 (m, 2H); 2.85 (m, 2H); 2.80 (d, 3H); 2.05-1.95 (m, 2H); 1.95-1.80 (m, 2H). | 104-106° C. | 420 |
| 27 | δ (ppm): 8.25 (d, 1H); 8.15 (d, 1H); 8.15 (s, 1H); 7.85 (s, 1H); 7.70 (t, 1H); 7.65 (m, 1H); 7.60 (d, 1H); 6.95 (d, 1H); 6.80 (s, 1H); 5.25 (s, 2H); 5.20 (m, 1H); 3.60 (m, 2H); 3.25 (m, 2H); 2.95 (m, 2H); 2.15 (m, 2H); 1.95 (m, 2H). | 185-187° C. | 456 |
| 28 | δ (ppm): 8.70 (s, 1H); 8.25 (d, 1H); 8.15 (d, 1H); 7.75 (t, 1H); 7.65 (t, 1H); 7.60 (d, 1H); 6.95 (d, 1H); 6.82 (s, 1H); 5.25 (s, 2H); 5.20 (m, 1H); 3.55 (m, 2H); 3.25 (m, 2H); 2.95 (m, 2H); 2.80 (d, 3H); 2.15 (m, 2H); 1.95 (m, 2H). | 131-133° C. | 470 |
| 29 | 9.10 (s, 1H); 8.25 (d, 1H); 8.15 (d, 1H); 7.75-7.60 (m, 4H); 7.00 (d, 1H); 5.20 (s, 2H); 4.90 (s, 1H); 3.70 (m, 1H); 3.60 (m, 1H); 3.30 (m, 2H); 2.90 (m, 2H); 2.20 (m, 1H); 1.90 (m, 2H); 1.55 (m, 1H). | oil | 429 |
| 30 | 9.10 (s, 1H); 7.70 (m, 1H); 7.60 (d, 2H); 7.35 (t, 1H); 7.20 (d, 1H); 7.10 (s, 1H); 7.00 (d, 2H); 6.90 (d, 1H); 5.20 (s, 2H); 4.90 (q, 1H); 4.10 (q, 2H); 3.60 (m, 2H); 3.30 (m, 2H); 3.05 (m, 1H); 2.80 (m, 1H); 2.10 (m, 1H); 1.85 (m, 1H); 1.55 (m, 1H); 1.35 (t, 3H) | oil | 465 |
| 31 | δ (ppm): 8.15 (s, 1H); 7.85 (s, 1H); 7.65 (t, 2H); 7.55 (d, 2H); 7.25 (t, 2H); 7.00 (d, 2H); 6.80 (s, 1H); 5.25 (s, 2H); 5.00 (m, 1H); 3.55 (m, 2H); 3.25 (m, 2H); 2.85 (m, 2H); 2.05 (m, 2H); 1.90 (m, 2H). | 200-201° C. | 464* |
| 32 | δ (ppm): 8.70 (s, 1H); 7.45 (d, 1H); 7.20 (m, 2H); 6.80 (s, 1H); | 104-106° C. | 438 |

TABLE 2-continued

| No. | $^1$H NMR 400 MHz DMSO | m.p. | M + H |
|---|---|---|---|
| | 5.25 (s, 2H); 4.95 (m, 1H); 3.55 (m, 2H); 3.20 (d, 2H); 2.85 (m, 2H); 2.80 (s, 3H); 2.05 (m, 2H); 1.90 (m, 2H). | | |
| 33 | δ (ppm): 8.10 (s, 1H); 7.85 (s, 1H); 7.40 (d, 1H); 7.20 (m, 6.80 (s, 1H); 5.25 (s, 2H); 5.00 (m, 1H); 3.55 (m, 2H); 3.25 (d, 2H); 2.85 (m, 2H); 2.05 (m, 2H); 1.85 (m, 2H). | 113-115° C. | 424 |
| 34 | δ (ppm): 8.15 (s, 1H); 7.85 (s, 1H); 7.45 (t, 1H); 7.05 (m, 1H); 6.80 (d, 2H); 5.25 (s, 2H); 5.00 (m, 1H); 3.55 (m, 2H); 3.20 (d, 2H); 2.85 (m, 2H); 2.00 (m, 2H); 1.90 (m, 2H). | 100-102° C. | 422* |
| 35 | δ (ppm): 8.70 (s, 1H); 7.45 (t, 1H); 7.05 (d, 1H); 6.80 (m, 2H); 5.25 (s, 2H); 4.95 (m, 1H); 3.55 (m, 2H); 3.20 (d, 2H); 2.85 (m, 2H); 2.80 (s, 3H); 2.00 (m, 2H); 1.90 (m, 2H). | 101-102° C. | 438 |
| 36 | δ (ppm): 8.10 (s, 1H); 7.85 (s, 1H); 7.55 (s, 1H); 7.35 (d, 1H); 7.15 (d, 1H); 6.80 (s, 1H); 5.25 (s, 2H); 5.05 (m, 1H); 3.55 (m, 2H); 3.20 (d, 2H); 2.85 (m, 2H); 2.00 (m, 2H); 1.85 (m, 2H). | 99-100° C. | 438 |
| 37 | δ (ppm): 8.70 (m, 1H); 7.55 (s, 1H); 7.35 (d, 1H); 7.15 (d, 1H); 6.80 (s, 1H); 5.25 (s, 2H); 5.05 (m, 1H); 3.55 (m, 2H); 3.25 (d, 2H); 2.85 (m, 2H); 2.80 (s, 3H); 2.05 (m, 2H); 1.85 (m, 2H). | 105-107° C. | 454 |
| 38 | δ (ppm): 9.20 (s, 1H); 8.40 (d, 1H); 8.15 (s, 1H); 7.90 (d, 1H); 7.85 (s, 1H); 7.75 (d, 1H); 7.50 (s, 1H); 7.40 (d, 1H); 6.85 (s, 1H); 5.25 (s, 2H); 5.15 (m, 1H); 3.60 (m, 2H); 3.25 (m, 2H); 2.90 (m, 2H); 2.10 (m, 2H); 2.00 (m, 2H). | 170-172° C. | 423 |
| 39 | δ (ppm): 9.15 (s, 1H); 8.40 (d, 1H); 8.15 (s, 1H); 8.00 (d, 1H); 7.85 (s, 1H); 7.70 (d, 1H); 7.30 (s, 1H); 7.25 (d, 1H); 6.80 (s, 1H); 5.25 (s, 2H); 5.15 (m, 1H); 3.60 (m, 2H); 3.25 (m, 2H); 2.85 (m, 2H); 2.10 (m, 2H); 2.00 (m, 2H). | 208-210° C. | 423 |
| 40 | δ (ppm): 8.15 (s, 1H); 7.90 (d, 1H); 7.85 (s, 1H); 7.40 (t, 1H); 7.35 (t, 1H); 6.80 (s, 1H); 6.45 (s, 1H); 5.25 (s, 2H); 3.65 (m, 2H); 3.45 (d, 2H); 3.00 (m, 2H); 2.50 (m, 2H); 2.00 (d, 2H). | 173-174° C. | 447 |
| 41 | δ (ppm): 8.60 (s, 1H); 7.70 (d, 2H); 7.65 (s, 1H); 7.50 (s, 1H); 7.20 (d, 2H); 6.95 (t, 2H); 5.20 (s, 2H); 5.05 (m, 1H); 4.15 (dq, 2H); 3.55 (m, 2H); 3.25 (m, 2H); 2.90 (m, 2H); 2.05 (m, 2H); 1.95 (m, 2H); 1.40 (t, 3H). | 166-168° C. | 466 |
| 42 | δ (ppm): 10.10 (broad s, 1H); 9.05 (t, 1H); 7.10 (t, 2H); 6.95 (m, 3H); 5.25 (s, 2H); 4.90 (m, 1H); 3.65 (m, 2H); 3.55 (m, 2H); 3.25 (m, 2H); 3.20 (m, 2H); 2.85 (s, 8H); 2.00 (m, 2H); 1.85 (m, 2H). | 146-148° C. (HCl) | 461 |
| 43 | δ (ppm): 8.60 (s, 1H); 8.25 (s, 1H); 7.70 (d, 2H); 7.20 (d, 2H); 6.95 (t, 2H); 5.20 (s, 2H); 5.05 (m, 1H); 4.15 (dq, 2H); 3.55 (m, 2H); 3.25 (m, 2H); 2.90 (m, 2H); 2.75 (d, 3H); 2.05 (m, 2H); 1.95 (m, 2H); 1.40 (t, 3H). | 130-132° C. | 480 |
| 44 | δ (ppm): 7.10 (t, 2H); 6.90 (d, 2H); 6.75 (s, 1H); 5.25 (s, 2H); 4.90 (m, 1H); 3.55 (m, 2H); 3.20 (d, 2H); 3.10 (s, 3H); 3.05 (s, 3H); 2.80 (m, 2H); 2.00 (m, 2H); 1.85 (m, 2H). | oil | 418 |
| 45 | δ (ppm): 8.70 (broad s, 1H); 7.65 (m, 2H); 7.55 (m, 2H); 7.22 (t, 2H); 6.98 (d, 2H); 6.82 (s, 1H); 5.25 (s, 2H); 5.00 (m, 1H); 3.50 (m, 2H); 3.21 (m, 2H); 2.85 (m, 2H); 2.78 (s, 3H); 2.05 (m, 2H); 1.90 (m, 2H). | 154-156° C. | 480 |

The compounds of the invention underwent pharmacological tests to determine their inhibitory effect on the enzyme FAAH (Fatty Acid Amide Hydrolase).

Protocol 1:

The inhibitory activity was demonstrated in a radioenzymatic test based on measuring the product of hydrolysis of anandamide [ethanolamine 1-$^3$H] with FAAH (*Life Sciences* (1995), 56, 1999-2005 and *Journal of Biochemical and Biophysical Methods* (2004), 60(2), 171-177). Thus, mouse brains (minus the cerebellum) are removed and stored at −80° C. The membrane homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in 96-well Multiscreen filtration plates in a final volume of 70 μL. Reaction buffer supplemented with fatty acid-free bovine serum albumin (BSA, 1 mg/ml) is used for the enzymatic reaction and the dilution of the compounds and of the anandamide [ethanolamine 1-$^3$H]. The reaction buffer containing BSA (43 μL/well), the diluted test compounds at different concentrations (7 μL/well containing 1% DMSO) and the membrane preparation (10 μL/well, i.e. 200 μg of tissue per test) are successively added to the wells. After preincubation for 20 minutes of the compounds with the enzyme at 25° C., the reaction is started by adding anandamide [ethanolamine 1-$^3$H] (specific activity of 15-20 Ci/mmol) diluted with cold anandamide (10 μL/well, final concentration of 10 μM, 0.01 μCi per test). After incubation for 20 minutes at 25° C., the enzymatic reaction is stopped by adding a 5M solution of active charcoal prepared in 1.5M NaCl buffer and 0.5 M HCl (50 μL/well). The mixture is stirred for 10 minutes and the aqueous phase containing the ethanolamine [1-$^3$H] is then recovered by filtration under vacuum and counted by liquid scintillation.

Protocol 2:

The inhibitory activity was demonstrated via a fluorescent technique in an enzymatic test based on measuring the fluorescent product of hydrolysis of arachidonoyl 7-amino-4-methylcoumarin amide (AAMC) with FAAH (Analytical Biochemistry (2005), 343:143-151, J. of Biomolecular Screening (2006), 11(5): 519-527 and J. of Neurosciences Methods (2007), 161: 47-54). Thus, mouse brains (minus the cerebellum) are withdrawn and stored at −80° C. The brain homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in black polystyrene 384-well plates in a final volume of 50 μL. Reaction buffer supplemented with fatty acid-free bovine serum albumin (BSA, 1 mg/ml) is used for the enzymatic reaction, the dilution of the compounds and the dilution of the AAMC. Reaction buffer containing the BSA (25 μL/well), the diluted test compounds at different concentrations (5 µL/well containing 1% DMSO) and the membrane preparation (10 µL/well, i.e. 200 µg of tissue per test) are successively added to the wells. After preincubation for 20 minutes of the compounds with the enzyme at 25° C., the reaction is started by adding 10 µL of substrate per well (AAMC, final concentration of 10 µM). After incubation for 40 minutes at 37° C., the aminomethyl coumarin (AMC) produced is measured by fluorescent counting (Envision plate reader).

Under the conditions of protocol 1, the compounds of the invention that are the most active have $IC_{50}$ values (concentration that inhibits 50% of the control enzymatic activity of FAAH) of between 0.001 and 1 µM. For example, compounds 3, 7, 12, 23, 28 and 34 have respective $IC_{50}$ values of 3.5 nM, 89 nM, 19 nM, 34 nM, 12 nM and 3.2 nM.

Under the conditions of protocol 2, the compounds of the invention that are the most active have $IC_{50}$ values (concentration that inhibits 50% of the control enzymatic activity of FAAH) of between 0.001 and 1 µM. For example, compounds 44 and 45 have respective $IC_{50}$ values of 7.4 nM and 0.47 nM.

It thus appears that the compounds according to the invention have inhibitory activity on the enzyme FAAH.

The in vivo activity of the compounds of the invention was evaluated in a test of analgesia.

Thus, the intraperitoneal (i.p.) administration of PBQ (phenylbenzoquinone, 2 mg/kg in 0.9% sodium chloride solution containing 5% ethanol) to male OF1 mice weighing 25 to 30 g causes abdominal stretching, on average 30 torsions or contractions within a period of 5 to 15 minutes after injection. The test compounds are administered orally (p.o.) or intraperitoneally (i.p.) suspended in Tween 80 at 0.5%, 60 minutes or 120 minutes before the administration of PBQ. Under these conditions, the compounds of the invention that are the most powerful reduce by 35% to 80% the number of stretches induced with PBQ, over a dose range of between 1 and 30 mg/kg.

For example, compounds 24 and 35 of Table 1 reduce by 50% the number of stretches induced with PBQ, at a dose of 30 mg/kg p.o. at 120 minutes.

The enzyme FAAH (*Chemistry and Physics of Lipids*, (2000), 108, 107-121) catalyses the hydrolysis of the endogenous derivatives of amides and esters of various fatty acids such as N-arachidonoylethanolamine (anandamide), N-palmitoyl-ethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue content of these endogenous substances. In this respect, they may be used in the prevention and treatment of pathologies in which the endogenous cannabinoids and/or any other substrate metabolized by the enzyme FAAH are involved. Mention may be made, for example, of the following diseases and complaints: pain, especially acute or chronic pain of neurogenic type: migraine, neuropathic pain including the forms associated with the herpes virus and diabetes and chemotherapy, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular postchemotherapy nausea, eating disorders, in particular anorexia and cachexia of diverse nature, neurological and psychiatric pathologies: tremor, dyskinaesia, dystonia, spasticity, compulsive and obsessive behaviour, Tourette's syndrome, all forms of depression and anxiety of any nature or origin, mood disorders, psychoses, acute and chronic neurodegenerative diseases: Parkinson's disease, Alzheimer's disease, senile dementia, Huntington's chorea, lesions associated with cerebral ischaemia and cranial and medullary trauma, epilepsy, sleeping disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (gliobastomas, medullo-epitheliomas, medullo-blastomas, neuroblastomas, tumours of embryonic origin, astrocytomas, astroblastomas, ependyomas, oligodendrogliomas, plexus tumour, neuroepitheliomas, pineal gland tumours, ependymoblastomas, malignant meningiomas, sarcomatoses, malignant melanomas, schwennomas), immune system disorders, especially autoimmune diseases: psoriasis, lupus erythematosus, connective tissue diseases, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hypersensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory pathway diseases, bronchospasms, coughing, asthma, chronic bronchitis, chronic obstruction of the respiratory pathways, emphysema, gastrointestinal diseases: irritable bowel syndrome, intestinal inflammatory disorders, ulcers, diarrhoea, urinary incontinence and inflammation of the bladder.

The use of the compounds according to the invention, in the form of the base, or a pharmaceutically acceptable acid-addition salt, hydrate or solvate, for the preparation of a medicinal product for treating the pathologies mentioned above forms an integral part of the invention.

A subject of the invention is also medicinal products comprising a compound of formula (I), or an acid-addition salt, or alternatively a pharmaceutically acceptable hydrate or solvate of the compound of formula (I). These medicinal products find their therapeutic use especially in the treatment of the pathologies mentioned above.

According to another of its aspects, the present invention relates to pharmaceutical compositions containing, as active principal, at least one compound according to the invention. These pharmaceutical compounds contain an effective dose of a compound according to the invention, or a pharmaceutically acceptable acid-addition salt, hydrate or solvate of the said compound, and optionally one or more pharmaceutically acceptable excipients.

The said excipients are chosen, according to the pharmaceutical form and the desired administration form, from the usual excipients known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principal of formula (I) above, or the possible acid-addition salt, solvate or hydrate thereof, may be administered in a unit administration form, as a mixture with standard pharmaceutical excipients, to man and animals for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular and intranasal administration forms, forms for administration by inhalation, subcutaneous, intramuscular or intravenous administration forms and rectal or vaginal administration forms. For topical administration, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principal per kg of body weight, depending on the presentation form.

There may be particular cases in which higher or lower doses are suitable, and such doses also form part of the invention. According to the usual practice, the dose that is suitable for each patient is determined by the doctor according to the mode of administration and the weight and response of the said patient.

According to another of its aspects, the invention also relates to a method for treating the pathologies mentioned above, which comprises the administration of an effective dose of a compound according to the invention, a pharmaceutically acceptable acid-addition salt thereof or a solvate or hydrate of the said compound.

The invention claimed is:

1. A compound corresponding to formula (I)

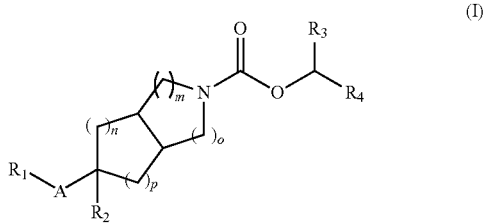

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

m, n, o and p represent, independently of each other, a number ranging from 0 to 3 and are such that each of m+o and n+p is less than or equal to 4;

A represents a covalent bond, an oxygen atom, a group $C_{1-6}$-alkylene or a group —O—$C_{1-6}$-alkylene in which the end represented by an oxygen atom is bonded to the group $R_1$ and the end represented by an alkylene group is bonded to the carbon of the bicycle;

$R_1$ represents a group $R_5$ optionally substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolyl, isoquinolyl, phthalazinyl, quinazolinyl, quinoxalinyl, cinnolinyl, naphthyridinyl, benzothiazolyl, benzoxazolyl, benzimidazolyl, benzisothiazolyl, bensisoxazolyl, indazolyl and benzotriazolyl;

$R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O— group;

$R_7$ represents a group chosen from phenyl, pyridyl, pyridazinyl, pyrimidinyl, pyrazinyl and triazinyl; the group(s) $R_7$ possibly being substituted with one or more groups $R_6$, which may be identical or different; the group(s) $R_7$ possibly being substituted with one or more groups $R_6$, which may be identical or different;

$R_3$ represents a hydrogen or fluorine atom, a group $C_{1-6}$-alkyl or a trifluoromethyl group;

$R_4$ represents a 5-membered heterocycle chosen from furyl, pyrrolyl, thienyl, thiazolyl, isothiazolyl, oxazolyl, isoxazolyl, pyrrazolyl, oxadiazolyl, thiadiazolyl, imidazole, triazolyl and tetrazolyl;

this heterocycle being unsubstituted or substituted with one or more substituents chosen from a halogen atom and a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)$($C_{1-3}$-alkylene-$NR_{10}R_{11}$), $SO_2R_8$, $SO_2NR_8R_9$ or —O—($C_{1-3}$-alkylene)-O—;

$R_8$, $R_9$, $R_{10}$ and $R_{11}$ represent, independently of each other, a hydrogen atom or a group $C_{1-6}$-alkyl, or form, with the atom(s) that bear them, in the case of $NR_8R_9$, a ring chosen from azetidine, pyrrolidine, piperidine, morpholine, thiomorpholine, azepine, oxazepine and piperazine rings, this ring being optionally substituted with a group $C_{1-6}$-alkyl or benzyl;

in the case of $NR_8COR_9$, a lactam ring; in the case of $NR_8CO_2R_9$, an oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring; or in the form of a base or of an acid-addition salt.

2. The compound of claim 1, wherein $R_2$ represents a hydrogen atom or a hydroxyl group; or in the form of a base or of an acid-addition salt.

3. The compound of claim 1 wherein m, n, o and p have the value 1, or alternatively m and o have the value 1, n has the value 0 and p has the value 2; or in the form of a base or of an acid-addition salt.

4. The compound of claim 1, wherein A represents a covalent bond or an oxygen atom; or in the form of a base or of an acid-addition salt.

5. The compound of claim 1, wherein $R_1$ represents a group $R_5$ that is unsubstituted or substituted with one or more groups $R_6$ and/or $R_7$;

$R_5$ represents a phenyl, naphthyl, benzothiazolyl or isoquinolyl group;

$R_6$ represents a halogen atom or a group $C_{1-6}$-haloalkyl or a group $C_{1-6}$-alkoxy;

$R_7$ represents a phenyl that may be substituted with one or more groups $R_6$, which may be identical or different; or in the form of a base or of an acid-addition salt.

6. The compound of claim 1, wherein $R_3$ represents a hydrogen atom; or in the form of a base or of an acid-addition salt.

7. The compound of claim 1, wherein $R_4$ represents a group chosen from a thiazolyl, a thiadiazolyl, a triazolyl, an oxazolyl and an isoxazolyl;

this group being unsubstituted or substituted with one or more groups $C_{1-6}$-alkyl, $CONR_8R_9$ or $CON(R_8)(C_{1-3}$-alkylene-$NR_{10}R_{11}$);

$R_8$, $R_9$, $R_{10}$ and $R_{11}$ represent, independently of each other, a hydrogen atom or a group $C_{1-6}$-alkyl; or in the form of a base or of an acid-addition salt.

8. The compound of claim 1 selected from the group consisting of:

thiazol-2-ylmethyl (3aR,5s,6aS)-5-(4-chlorophenoxy)hexahydrocyclopenta[c]pyrrole-2(1H)-carboxylate (exo)

thiazol-2-ylmethyl (3aR,5s,6aS)-5-[4-(trifluoromethyl)phenoxy]hexahydrocyclopenta[c]pyrrole-2(1H)-carboxylate (exo)

thiazol-2-ylmethyl (3aR,5s,6aS)-5-[(7-ethoxy-2-naphthyl)oxy]hexahydrocyclopenta[c]pyrrole-2(1H)-carboxylate (exo)

thiazol-2-ylmethyl (3aR,5r,6aS)-5-[3-(trifluoromethyl)phenoxy]hexahydrocyclopenta[c]pyrrole-2(1H)-carboxylate (endo)

thiazol-2-ylmethyl (3aR,5s,6aS)-5-[3-(trifluoromethyl)phenoxy]hexahydrocyclopenta[c]pyrrole-2(1R)-carboxylate (exo)

thiazol-2-ylmethyl (3aR,5r,6aS)-5-[(4'-ethoxybiphenyl-3-yl)oxy]hexahydrocyclopenta[c]pyrrole-2(1H)-carboxylate (endo)

1,2,3-thiadiazol-4-ylmethyl (3aR,5s,6aS)-5-(4-chlorophenoxy)hexahydrocyclopenta[c]pyrrole-2(1H)-carboxylate (exo)

(5-tert-butyl-1,3,4-thiadiazol-2-yl)methyl (3aR,5s,6aS)-5-(4-chlorophenoxy)hexahydrocyclopenta[c]pyrrole-2(1H)-carboxylate (exo)

1,2,3-thiadiazol-4-ylmethyl (3aR,5s,6aS)-(4-fluorophenoxy)hexahydrocyclopenta[c]pyrrole-2(1H)-carboxylate (exo)

(3-carbamoylisoxazol-5-yl)methyl (3aR,5s,6aS)-5-(4-fluorophenoxy)hexahydrocyclopenta[c]pyrrole-2(1H)-carboxylate (exo)

[3-(methylcarbamoyl)isoxazol-5-yl]methyl (3aR,5s,6aS)-5-(4-fluorophenoxy)hexahydrocyclopenta[c]pyrrole-2(1H)-carboxylate (exo)

(3-carbamoylisoxazol-5-yl)methyl (3aR,5s,6aS)-5-(4-chlorophenoxy)hexahydrocyclopenta[c]pyrrole-2(1H)-carboxylate (exo)

(1-methyl-1H-1,2,4-triazol-5-yl)methyl (3aR,5s,6aS)-5-(4-chlorophenoxy)hexahydrocyclopenta[c]pyrrole-2(1H)-carboxylate (exo)

(4-carbamoylthiazol-2-yl)methyl (3aR,5s,6aS)-5-(4-chlorophenoxy)hexahydrocyclopenta[c]pyrrole-2(1H)-carboxylate (exo)

[4-(methylcarbamoyl)thiazol-2-yl]methyl (3aR,5s,6aS)-5-(4-chlorophenoxy)hexahydrocyclopenta[c]pyrrole-2(1H)-carboxylate (exo)

(3-carbamoylisoxazol-5-yl)methyl (3aR,5s,6aS)-5-[3-(trifluoromethyl)phenoxy]hexahydrocyclopenta[c]pyrrole-2(1H)-carboxylate (exo)

[3-(methylcarbamoyl)isoxazol-5-yl]methyl (3aR,5s,6aS)-5-[3-(trifluoromethyl)phenoxy]hexahydrocyclopenta[c]pyrrole-2(1H)-carboxylate (exo)

thiazol-2-ylmethyl (3aR,5s,6aS)-5-[(4'-ethoxybiphenyl-3-yl)oxy]hexahydrocyclopenta[c]pyrrole-2(1H)-carboxylate (exo)

(4-carbamoyloxazol-2-yl)methyl (3aR,5s,6aS)-5-(4-chlorophenoxy)hexahydrocyclopenta[c]pyrrole-2(1H)-carboxylate (exo)

thiazol-4-ylmethyl (3aR,4S,6aS)-4-[(6-methoxy-2-naphthyl)oxy]hexahydrocyclopenta[c]pyrrole-2(1H)-carboxylate (exo)

thiazol-4-ylmethyl (3aR,4R,6aS)-4-[3-(trifluoromethyl)phenoxy]hexahydrocyclopenta[c]pyrrole-2(1H)-carboxylate (endo)

(4-carbamoylthiazol-2-yl)methyl (3aR,5s,6aS)-5-[(7-ethoxy-2-naphthyl)oxy]hexahydrocyclopenta[c]pyrrole-2(1H)-carboxylate (exo)

[4-(methylcarbamoyl)thiazol-2-yl]methyl (3aR,5s,6aS)-5-[(7-ethoxy-2-naphthyl)oxy]hexahydrocyclopenta[c]pyrrole-2(1H)-carboxylate (exo)

(3-carbamoylisoxazol-5-yl)methyl (3aR,5s,6aS)-5-[(7-ethoxy-2-naphthyl)oxy]hexahydrocyclopenta[c]pyrrole-2(1H)-carboxylate (exo)

[3-(methylcarbamoyl)isoxazol-5-yl]methyl (3aR,5s,6aS)-5-[(7-ethoxy-2-naphthyl)oxy]hexahydrocyclopenta[c]pyrrole-2(1H)-carboxylate (exo)

[4-(methylcarbamoyl)oxazol-2-yl]methyl (3aR,5s,6aS)-5-(4-chlorophenoxy)hexahydrocyclopenta[c]pyrrole-2(1H)-carboxylate (exo)

(3-carbamoylisoxazol-5-yl)methyl (3aR,5s,6aS)-5-[(4-chloro-1-naphthyl)oxy]hexahydrocyclopenta[c]pyrrole-2(1H)-carboxylate (exo)

[3-(methylcarbamoyl)isoxazol-5-yl]methyl (3aR,5s,6aS)-5-[(4-chloro-1-naphthyl)oxy]hexahydrocyclopenta[c]pyrrole-2(1H)-carboxylate (exo)

thiazol-4-ylmethyl (3aR,4S,6aS)-4-[(4-chloro-1-naphthyl)oxy]hexahydrocyclopenta[c]pyrrole-2(1H)-carboxylate (exo)

thiazol-4-ylmethyl (3aR,4R,6aS)-4-[(4'-ethoxybiphenyl-3-yl)oxy]hexahydrocyclopenta[c]pyrrole-2(1H)-carboxylate (endo)

(3-carbamoylisoxazol-5-yl)methyl (3aR,5s,6aS)-5-[(4'-fluorobiphenyl-4-yl)oxy]hexahydrocyclopenta[c]pyrrole-2(1H)-carboxylate (exo)

[3-(methylcarbamoyl)isoxazol-5-yl]methyl (3aR,5s,6aS)-5-(4-chloro-2-fluorophenoxy)hexahydrocyclopenta[c]pyrrole-2(1H)-carboxylate (exo)

(3-carbamoylisoxazol-5-yl)methyl (3aR,5s,6aS)-5-(4-chloro-2-fluorophenoxy)hexahydrocyclopenta[c]pyrrole-2(1H)-carboxylate (exo)

(3-carbamoylisoxazol-5-yl)methyl (3aR,5s,6aS)-5-(4-chloro-3-fluorophenoxy)hexahydrocyclopenta[c]pyrrole-2(1H)-carboxylate (exo)

[3-(methylcarbamoyl)isoxazol-5-yl]methyl (3aR,5s,6aS)-5-(4-chloro-3-fluorophenoxy)hexahydrocyclopenta[c]pyrrole-2(1H)-carboxylate (exo)

(3-carbamoylisoxazol-5-yl)methyl (3aR,5s,6aS)-5-(2,4-dichlorophenoxy)hexahydrocyclopenta[c]pyrrole-2(1H)-carboxylate (exo)

[3-(methylcarbamoyl)isoxazol-5-yl]methyl (3aR,5s,6aS)-5-(2,4-dichlorophenoxy)hexahydrocyclopenta[c]pyrrole-2(1H)-carboxylate (exo)

(3-carbamoylisoxazol-5-yl)methyl (3aR,5s,6aS)-5-(isoquinolin-7-yloxy)hexahydrocyclopenta[c]pyrrole-2(1H)-carboxylate (exo)

(3-carbamoylisoxazol-5-yl)methyl (3aR,5s,6aS)-5-(isoquinolin-6-yloxy)hexahydrocyclopenta[c]pyrrole-2(1H)-carboxylate (exo)

(3-carbamoylisoxazol-5-yl)methyl (3aR,5r,6aS)-5-(4-fluoro-1,3-benzothiazol-2-yl)-5-hydroxyhexahydrocyclopenta[c]pyrrole-2(1H)-carboxylate (exo)

(4-carbamoyloxazol-2-yl)methyl (3aR,5s,6aS)-5-[(7-ethoxy-2-naphthyl)oxy]hexahydrocyclopenta[c]pyrrole-2(1H)-carboxylate (exo)

(3-{[2-(dimethylamino)ethyl]carbamoyl}isoxazol-5-yl) methyl (3aR,5s,6aS)-5-(4-fluorophenoxy)-hexahydro-cyclopenta[c]pyrrole-2(1H)-carboxylate (exo), and its hydrochloride

[4-(methylcarbamoyl)oxazol-2-yl]methyl (3aR,5s,6aS)-5-[(7-ethoxy-2-naphthyl)oxy]hexahydrocyclopenta[c]pyrrole-2(1H)-carboxylate (exo)

(3-dimethylcarbamoylisoxazol-5-yl)methyl (3aR,5s,6aS)-5-(4-fluorophenoxy)hexahydrocyclopenta[c]pyrrole-2(1H)-carboxylate (exo)

(3-methylcarbamoylisoxazol-5-yl)methyl (3aR,5s,6aS)-5-[(4'-fluorobiphenyl-4-yl)oxy]hexahydrocyclopenta[c]pyrrole-2(1H)-carboxylate (exo).

9. A pharmaceutical composition comprising the compound of claim 1, in the form of the base or of a pharmaceutically acceptable acid-addition salt.

10. The pharmaceutical composition of claim 9, further comprising one or more pharmaceutically acceptable excipients.

* * * * *